US008541351B2

(12) United States Patent
Thompson et al.

(10) Patent No.: US 8,541,351 B2
(45) **Date of Patent: *Sep. 24, 2013**

(54) ESTOLIDE COMPOSITIONS EXHIBITING HIGH OXIDATIVE STABILITY

(71) Applicant: Biosynthetic Technologies, LLC, Irvine, CA (US)

(72) Inventors: Travis Thompson, Anaheim, CA (US); Jakob Bredsguard, Lake Forest, CA (US); Jeremy Forest, Irvine, CA (US)

(73) Assignee: Biosynthetic Technologies, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/705,543

(22) Filed: Dec. 5, 2012

(65) Prior Publication Data

US 2013/0102510 A1 Apr. 25, 2013

Related U.S. Application Data

(63) Continuation of application No. 13/483,602, filed on May 30, 2012, now Pat. No. 8,372,301.

(60) Provisional application No. 61/498,499, filed on Jun. 17, 2011, provisional application No. 61/569,046, filed on Dec. 9, 2011, provisional application No. 61/643,072, filed on May 4, 2012.

(51) Int. Cl.
*C07C 55/02* (2006.01)

(52) U.S. Cl.
USPC .............................. 508/506; 508/496; 252/68

(58) Field of Classification Search
USPC .................................. 252/68; 508/496, 506
See application file for complete search history.

(56) References Cited

U.S. PATENT DOCUMENTS

| | | | | |
|---|---|---|---|---|
| 2,049,072 | A | 7/1936 | Mikeska et al. | |
| 2,652,411 | A | 9/1953 | Teeter et al. | |
| 2,862,884 | A | 12/1958 | Dilworth et al. | |
| 4,428,850 | A | 1/1984 | Zoleski et al. | |
| 5,380,894 | A | 1/1995 | Burg et al. | |
| 5,451,332 | A | 9/1995 | Lawate | |
| 6,018,063 | A | 1/2000 | Isbell et al. | |
| 6,316,649 | B1 | 11/2001 | Cermak et al. | |
| 7,252,779 | B2 | 8/2007 | Mosier et al. | |
| 7,651,641 | B2 | 1/2010 | Corkran et al. | |
| 7,666,828 | B2 | 2/2010 | Bernhardt et al. | |
| 8,236,194 | B1 * | 8/2012 | Bredsguard et al. | 252/68 |
| 8,273,694 | B2 * | 9/2012 | Brown et al. | 508/496 |
| 8,287,754 | B1 | 10/2012 | Bredsguard et al. | |
| 8,372,301 | B2 * | 2/2013 | Bredsguard et al. | 252/68 |
| 8,399,389 | B2 | 3/2013 | Bredsguard et al. | |
| 2002/0017629 | A1 | 2/2002 | Mosier et al. | |
| 2002/0193262 | A1 | 12/2002 | Kaimai et al. | |
| 2004/0014615 | A1 | 1/2004 | Gao et al. | |
| 2004/0046146 | A1 | 3/2004 | Ankner et al. | |
| 2004/0053794 | A1 | 3/2004 | Baba | |
| 2007/0092475 | A1 | 4/2007 | Wohlman | |
| 2007/0161832 | A1 | 7/2007 | Myllyoja et al. | |
| 2008/0020956 | A1 | 1/2008 | Mosier et al. | |
| 2009/0159835 | A1 | 6/2009 | Kramer et al. | |
| 2009/0159837 | A1 | 6/2009 | Kramer et al. | |
| 2010/0120643 | A1 | 5/2010 | Brown et al. | |
| 2010/0184855 | A1 | 7/2010 | Bernhardt et al. | |
| 2011/0105814 | A1 | 5/2011 | Koivusalmi et al. | |
| 2011/0294174 | A1 | 12/2011 | Franklin et al. | |

(Continued)

FOREIGN PATENT DOCUMENTS

| | | |
|---|---|---|
| WO | WO-99/25794 | 5/1999 |
| WO | WO-01/53247 A1 | 7/2001 |
| WO | WO-2011/037778 A1 | 3/2011 |
| WO | WO-2011/106186 A1 | 9/2011 |

OTHER PUBLICATIONS

Cermak et al, "Improved oxidative stability of estolide esters," *Indus. Crops and Prods.*, 18: 223-230 (2003).

(Continued)

*Primary Examiner* — Douglas McGinty
(74) *Attorney, Agent, or Firm* — Jeremy Forest

(57) ABSTRACT

Provided herein are estolide compositions having high oxidative stability, said compositions comprising at least one compound of formula:

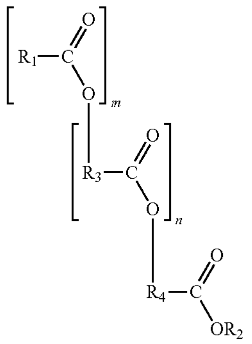

in which n is an integer equal to or greater than 0; m is an integer equal to or greater than 1; $R_1$, independently for each occurrence, is selected from optionally substituted alkyl that is saturated or unsaturated, and branched or unbranched; $R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched. Also provided herein are uses for the compositions and methods of preparing the same.

24 Claims, No Drawings

(56) References Cited

U.S. PATENT DOCUMENTS

| | | | | |
|---|---|---|---|---|
| 2012/0018667 | A1 | 1/2012 | Krammer et al. | |
| 2012/0083435 | A1 | 4/2012 | Bredsguard | |
| 2012/0119862 | A1* | 5/2012 | Franklin et al. | 336/58 |
| 2012/0172269 | A1 | 7/2012 | Greaves et al. | |
| 2012/0172609 | A1 | 7/2012 | Bredsguard et al. | |
| 2012/0178660 | A1 | 7/2012 | Bredsguard | |

OTHER PUBLICATIONS

Cermak et al., "Comparison of a New Estolide Oxidative Stability Package," *J. Am. Oil Chem. Soc.*, 85: 879-885 (2008).

Dunn, "Effect of antioxidants on the oxidative stability of methyl soyate (biodiesel)," *Fuel Process. Tech.*, 86: 1071-1085 (2005).

Cermak et al., "Physical properties of saturated estolides and their 2-ethylhexyl esters," 16: 119-27 (2002).

Cermak et al., "Synthesis and physical properties of estolides from lesquerella and castor fatty acid esters," Indus. Crops and Prods., 23: 256-63 (2006).

Cermak et al., "Synthesis and Physical Properties of Tallow-Oleic Estolide 2-Ethylhexyl Esters," J. Amer. Oil Chem. Soc., 84(5): 449-56 (2007).

Isbell et al., "Physical properties of estolides and their ester derivatives," Indus. Crops and Prods., 13: 11-20 (2001).

Isbell et al., "Physical properties of triglyceride estolides from lesquerella and castor oils," Indus. Crops and Prods., 23: 256-253 (2006).

Rudnick, *Synthetics, Mineral Oils, and Bio-Based Lubricants*, CRC Press, Boca Raton, FL., Ch. 22, pp. 371-374 (2006).

Zerkowski, J., "Estolides: From structure and function to structured and functionalized," Lipid Tech., 20(11): 253-56 (2008).

International Search Report and Written Opinion for co-pending application PCT/US2012/026538, mailed Apr. 26, 2012.

International Search Report and Written Opinion for co-pending application PCT/US2012/039937, mailed Aug. 6, 2012.

Article 19 Amendments and Letter Accompanying Replacement Sheets for counterpart application PCT/US2012/026538, filed May 17, 2012.

Informal Comments filed in response to International Search Report and Written Opinion for counterpart application PCT/US2012/026538, filed May 17, 2012.

Co-Pending U.S. Appl. No. 13/587,120, filed Aug. 16, 2012.

Co-Pending U.S. Appl. No. 13/754,775, filed Jan. 30, 2013.

Office Action dated Sep. 14, 2012, for U.S. Appl. No. 13/483,602, filed May 30, 2012.

Notice of Allowance dated Dec. 3, 2012, for U.S. Appl. No. 13/483,602, filed May 30, 2012.

* cited by examiner

ESTOLIDE COMPOSITIONS EXHIBITING HIGH OXIDATIVE STABILITY

CROSS REFERENCE TO RELATED APPLICATIONS

This application is a continuation of U.S. patent application Ser. No. 13/483,602, filed May 30, 2012, which claims the benefit under 35 U.S.C. §119(e) of U.S. Provisional Patent Application No. 61/498,499, filed Jun. 17, 2011, U.S. Provisional Application No. 61/569,046, filed Dec. 9, 2011, and U.S. Provisional Patent Application No. 61/643,072, filed May 4, 2012, which are incorporated herein by reference in their entireties for all purposes.

FIELD

The present disclosure relates to lubricating compositions comprising one or more estolide compounds and exhibiting high oxidation stability, and methods of making the same.

BACKGROUND

A variety of commercial uses for fatty esters such as triglycerides have been described. When used as a lubricant, for example, fatty esters can provide a biodegradable alternative to petroleum-based lubricants. However, naturally-occurring fatty esters are typically deficient in one or more areas, including hydrolytic stability and/or oxidative stability.

SUMMARY

Described herein are estolide compositions exhibiting high oxidative stability, and methods of making and using the same.

In certain embodiments, the composition comprises at least one estolide compound of Formula I:

Formula I

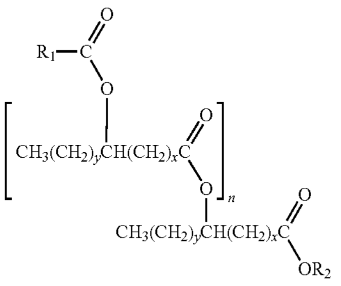

wherein x is, independently for each occurrence, an integer selected from 0, 1, 2, 3, 4, 5, 6, 7, 8, 9, 10, 11, 12, 13, 14, 15, 16, 17, 18, 19, and 20;

y is, independently for each occurrence, an integer selected from 0, 1, 2, 3, 4, 5, 6, 7, 8, 9, 10, 11, 12, 13, 14, 15, 16, 17, 18, 19, and 20;

n is an integer selected from 0, 1, 2, 3, 4, 5, 6, 7, 8, 9, 10, 11, and 12;

$R_1$ is an optionally substituted alkyl that is saturated or unsaturated, and branched or unbranched; and $R_2$ is selected from hydrogen and optionally substituted alkyl that is saturated or unsaturated, and branched or unbranched;

wherein each fatty acid chain residue of said at least one compound is independently optionally substituted.

In certain embodiments, the composition comprises at least one estolide compound of Formula II:

Formula II

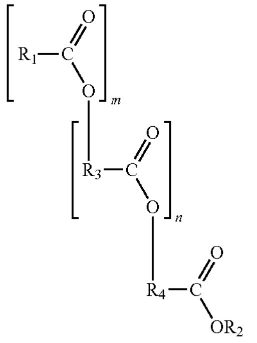

wherein m is an integer equal to or greater than 1;

n is an integer equal to or greater than 0;

$R_1$, independently for each occurrence, is an optionally substituted alkyl that is saturated or unsaturated, and branched or unbranched;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched.

In certain embodiments, the composition comprises at least one estolide compound of Formula III:

Formula III

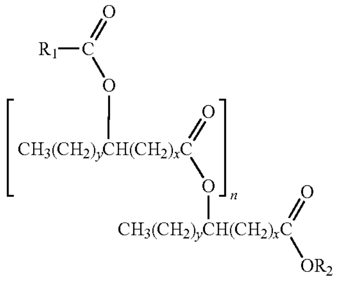

wherein x is, independently for each occurrence, an integer selected from 0, 1, 2, 3, 4, 5, 6, 7, 8, 9, 10, 11, 12, 13, 14, 15, 16, 17, 18, 19, and 20;

y is, independently for each occurrence, an integer selected from 0, 1, 2, 3, 4, 5, 6, 7, 8, 9, 10, 11, 12, 13, 14, 15, 16, 17, 18, 19, and 20;

n is an integer equal to or greater than 0;

$R_1$ is an optionally substituted alkyl that is saturated or unsaturated, and branched or unbranched; and $R_2$ is selected from hydrogen and optionally substituted alkyl that is saturated or unsaturated, and branched or unbranched;

wherein each fatty acid chain residue of said at least one compound is independently optionally substituted.

DETAILED DESCRIPTION

The estolide compositions described herein may exhibit superior oxidative stability when compared to other lubricant and/or estolide-containing compositions. Exemplary compositions include, but are not limited to, coolants, fire-resistant and/or non-flammable fluids, dielectric fluids such as transformer fluids, greases, drilling fluids, crankcase oils, hydraulic fluids, passenger car motor oils, 2- and 4-stroke lubricants, metalworking fluids, food-grade lubricants, refrigerating fluids, compressor fluids, and plasticized compositions.

The use of lubricants and lubricating fluid compositions may result in the dispersion of such fluids, compounds, and/or compositions in the environment. Petroleum base oils used in common lubricant compositions, as well as additives, are typically non-biodegradable and can be toxic. The present disclosure provides for the preparation and use of compositions comprising partially or fully bio-degradable base oils, including base oils comprising one or more estolides.

In certain embodiments, the lubricants and/or compositions comprising one or more estolides are partially or fully biodegradable and thereby pose diminished risk to the environment. In certain embodiments, the lubricants and/or compositions meet guidelines set for by the Organization for Economic Cooperation and Development (OECD) for degradation and accumulation testing. The OECD has indicated that several tests may be used to determine the "ready biodegradability" of organic chemicals. Aerobic ready biodegradability by OECD 301D measures the mineralization of the test sample to $CO_2$ in closed aerobic microcosms that simulate an aerobic aquatic environment, with microorganisms seeded from a waste-water treatment plant. OECD 301D is considered representative of most aerobic environments that are likely to receive waste materials. Aerobic "ultimate biodegradability" can be determined by OECD 302D. Under OECD 302D, microorganisms are pre-acclimated to biodegradation of the test material during a pre-incubation period, then incubated in sealed vessels with relatively high concentrations of microorganisms and enriched mineral salts medium. OECD 302D ultimately determines whether the test materials are completely biodegradable, albeit under less stringent conditions than "ready biodegradability" assays.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —C(O)$NH_2$ is attached through the carbon atom.

"Alkoxy" by itself or as part of another substituent refers to a radical —$OR^{31}$ where $R^{31}$ is alkyl, cycloalkyl, cycloalkylalkyl, aryl, or arylalkyl, which can be substituted, as defined herein. In some embodiments, alkoxy groups have from 1 to 8 carbon atoms. In some embodiments, alkoxy groups have 1, 2, 3, 4, 5, 6, 7, or 8 carbon atoms. Examples of alkoxy groups include, but are not limited to, methoxy, ethoxy, propoxy, butoxy, cyclohexyloxy, and the like.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl(allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

Unless otherwise indicated, the term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 40 carbon atoms, in certain embodiments, from 1 to 22 or 1 to 18 carbon atoms, in certain embodiments, from 1 to 16 or 1 to 8 carbon atoms, and in certain embodiments from 1 to 6 or 1 to 3 carbon atoms. In certain embodiments, an alkyl group comprises from 8 to 22 carbon atoms, in certain embodiments, from 8 to 18 or 8 to 16. In some embodiments, the alkyl group comprises from 3 to 20 or 7 to 17 carbons. In some embodiments, the alkyl group comprises 1, 2, 3, 4, 5, 6, 7, 8, 9, 10, 11, 12, 13, 14, 15, 16, 17, 18, 19, 20, 21, or 22 carbon atoms.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered non-aromatic heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. In certain embodiments, an aryl group can comprise 5, 6, 7, 8, 9, 10, 11, 12, 13, 14, 15, 16, 17, 18, 19, or 20 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl, or alkynyl moiety of the arylalkyl group is $C_{1-10}$ and the aryl moiety is $C_{6-20}$, and in certain embodiments, an arylalkyl group is $C_{7-20}$ arylalkyl, e.g., the alkanyl, alkenyl, or alkynyl moiety of the arylalkyl group is $C_{1-8}$ and the aryl moiety is $C_{6-12}$.

Estolide "base oil" and "base stock", unless otherwise indicated, refer to any composition comprising one or more estolide compounds. It should be understood that an estolide "base oil" or "base stock" is not limited to compositions for a particular use, and may generally refer to compositions comprising one or more estolides, including mixtures of estolides. Estolide base oils and base stocks can also include compounds other than estolides.

"Antioxidant" refers to a substance that is capable of inhibiting, preventing, reducing, or ameliorating oxidative reactions in another substance (e.g., base oil such as an estolide compound) when the antioxidant is used in a composition (e.g., lubricant formulation) that includes such other substances. An example of an "antioxidant" is an oxygen scavenger.

"Compounds" refers to compounds encompassed by structural Formula I, II, and III herein and includes any specific compounds within the formula whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure. "Achiral compounds" are compounds which are not chiral.

Compounds of Formula I, II, and III include, but are not limited to, optical isomers of compounds of Formula I, II, and III, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished by, for example, chromatography, using, for example a chiral high-pressure liquid chromatography (HPLC) column. However, unless otherwise stated, it should be assumed that Formula I, II, and III cover all asymmetric variants of the compounds described herein, including isomers, racemates, enantiomers, diastereomers, and other mixtures thereof. In addition, compounds of Formula I, II and III include Z- and E-forms (e.g., cis- and trans-forms) of compounds with double bonds. The compounds of Formula I, II, and III may also exist in several tautomeric forms including the enol form, the keto form, and mixtures thereof. Accordingly, the chemical structures depicted herein encompass all possible tautomeric forms of the illustrated compounds.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl. In certain embodiments, a cycloalkyl group is a $C_5$, $C_6$, $C_7$, $C_8$, $C_9$, $C_{10}$, $C_{11}$, $C_{12}$, $C_{13}$, $C_{14}$, or $C_{15}$ cycloalkyl.

"Cycloalkylalkyl" by itself or as part of another substituent refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Halogen" refers to a fluoro, chloro, bromo, or iodo group.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments, a heteroaryl group is a 5-, 6-, 7-, 8-, 9-, 10-, 11-, 12-, 13-, 14-, 15-, 16-, 17-, 18-, 19-, or 20-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or $sp^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Mixture" refers to a collection of molecules or chemical substances. Each component in a mixture can be independently varied. A mixture may contain, or consist essentially of, two or more substances intermingled with or without a constant percentage composition, wherein each component may or may not retain its essential original properties, and where molecular phase mixing may or may not occur. In mixtures, the components making up the mixture may or may not remain distinguishable from each other by virtue of their chemical structure.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Substituted" refers to a group in which one or more hydrogen atoms are independently replaced with the same or different substituent(s). Examples of substituents include, but are not limited to, $—R^{64}$, $—R^{60}$, $—O^-$, —OH, =O, $—OR^{60}$, $—SR^{60}$, $—S^-$, =S, $—NR^{60}R^{61}$, $=NR^{60}$, —CN, $—CF_3$, —OCN, —SCN, —NO, $—NO_2$, $=N_2$, $—N_3$, $—S(O)_2O^-$, $—S(O)_2OH$, $—S(O)_2R^{60}$, $—OS(O_2)O^-$, $—OS(O)_2R^{60}—P(O)(OR^{60})(O^-)$, $—OP(O)(OR^{60})(OR^{61})$, $—C(O)R^{60}$, $—C(S)R^{60}$, $—C(O)OR^{60}$, $—C(O)NR^{60}R^{61}$, $—C(O)O^-$, $—C(S)OR^{60}$, $—NR^{62}C(O)NR^{60}R^{61}$, $—NR^{62}C(S)NR^{60}R^{61}$, $NR^{62}C(NR^{63})NR^{60}R^{61}$, $—C(NR^{62})NR^{60}R^{61}$, $—S(O)_2$, $NR^{60}R^{61}$, $—NR^{63}S(O)_2R^{60}$, $—NR^{63}C(O)R^{60}$, and $—S(O)R^{60}$;

wherein each $—R^{64}$ is independently a halogen; each $R^{60}$ and $R^{61}$ are independently alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded form a heterocycloalkyl, substituted heterocycloalkyl, heteroaryl, or substituted heteroaryl ring, and $R^{62}$ and $R^{63}$ are independently alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, or substituted heteroarylalkyl, or $R^{62}$ and $R^{63}$ together with the atom to which they are bonded form one or more heterocycloalkyl, substituted heterocycloalkyl, heteroaryl, or substituted heteroaryl rings;

wherein the "substituted" substituents, as defined above for $R^{60}$, $R^{61}$, $R^{62}$, and $R^{63}$, are substituted with one or more, such as one, two, or three, groups independently selected from alkyl, -alkyl-OH, —O-haloalkyl, -alkyl-$NH_2$, alkoxy, cycloalkyl, cycloalkylalkyl, heterocycloalkyl, heterocycloalkylalkyl, aryl, heteroaryl, arylalkyl, heteroarylalkyl, —$O^-$, —OH, =O, —O-alkyl, —O-aryl, —O-heteroarylalkyl, —O-cycloalkyl, —O-heterocycloalkyl, —SH, —$S^-$, =S, —S-alkyl, —S-aryl, —S-heteroarylalkyl, —S-cycloalkyl, —S-heterocycloalkyl, —$NH_2$, =NH, —CN, —$CF_3$, —OCN, —SCN, —NO, —$NO_2$, =$N_2$, —$N_3$, —$S(O)_2O$, —$S(O)_2$, —$S(O)_2OH$, —$OS(O_2)O^-$, —$SO_2$(alkyl), —$SO_2$(phenyl), —$SO_2$(haloalkyl), —$SO_2NH_2$, —$SO_2NH$(alkyl), —$SO_2NH$(phenyl), —$P(O)(O^-)_2$, —P(O)(O-alkyl)($O^-$), —OP(O)(O-alkyl)(O-alkyl), —$CO_2H$, —C(O)O(alkyl), —CON(alkyl)(alkyl), —CONH(alkyl), —$CONH_2$, —C(O)(alkyl), —C(O)(phenyl), —C(O)(haloalkyl), —OC(O)(alkyl), —N(alkyl)(alkyl), —NH(alkyl), —N(alkyl)(alkylphenyl), —NH(alkylphenyl), —NHC(O)(alkyl), —NHC(O)(phenyl), —N(alkyl)C(O)(alkyl), and —N(alkyl)C(O)(phenyl).

As used in this specification and the appended claims, the articles “a,” “an,” and “the” include plural referents unless expressly and unequivocally limited to one referent.

All numerical ranges herein include all numerical values and ranges of all numerical values within the recited range of numerical values.

The present disclosure relates to estolide compounds, compositions and methods of making the same. In certain embodiments, the present disclosure also relates to estolide compounds, compositions comprising estolide compounds, the synthesis of such compounds, and the formulation of such compositions. In certain embodiments, the present disclosure relates to biosynthetic estolides having desired viscometric properties, while retaining or even improving other properties such as oxidative stability and pour point. In certain embodiments, new methods of preparing estolide compounds exhibiting such properties are provided. The present disclosure also relates to lubricant comprising certain estolide compounds.

In certain embodiments the composition comprises at least one estolide compound of Formula I:

Formula I

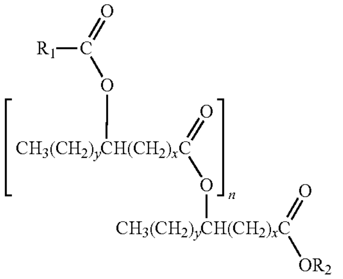

wherein x is, independently for each occurrence, an integer selected from 0, 1, 2, 3, 4, 5, 6, 7, 8, 9, 10, 11, 12, 13, 14, 15, 16, 17, 18, 19, and 20;

y is, independently for each occurrence, an integer selected from 0, 1, 2, 3, 4, 5, 6, 7, 8, 9, 10, 11, 12, 13, 14, 15, 16, 17, 18, 19, and 20;

n is an integer selected from 0, 1, 2, 3, 4, 5, 6, 7, 8, 9, 10, 11, and 12;

$R_1$ is an optionally substituted alkyl that is saturated or unsaturated, and branched or unbranched; and $R_2$ is selected from hydrogen and optionally substituted alkyl that is saturated or unsaturated, and branched or unbranched;

wherein each fatty acid chain residue of said at least one compound is independently optionally substituted.

In certain embodiments the composition comprises at least one estolide compound of Formula II:

Formula II

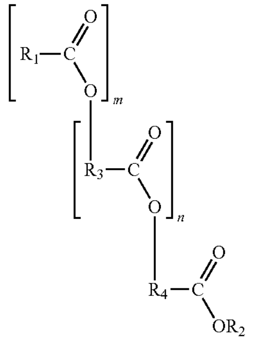

wherein m is an integer greater than or equal to 1;

n is an integer greater than or equal to 0;

$R_1$, independently for each occurrence, is an optionally substituted alkyl that is saturated or unsaturated, and branched or unbranched;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched.

In certain embodiments the composition comprises at least one estolide compound of Formula III:

Formula III

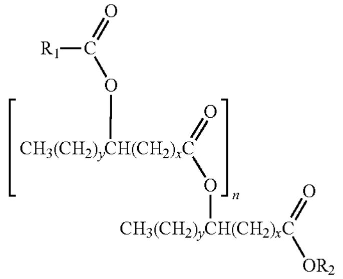

wherein x is, independently for each occurrence, an integer selected from 0 to 20;

y is, independently for each occurrence, an integer selected from 0 to 20;

n is an integer greater than or equal to 0;

$R_1$ is an optionally substituted alkyl that is saturated or unsaturated, and branched or unbranched; and $R_2$ is selected from hydrogen and optionally substituted alkyl that is saturated or unsaturated, and branched or unbranched;

wherein each fatty acid chain residue of said at least one compound is independently optionally substituted.

In certain embodiments, the composition comprises at least one estolide compound of Formula I, II, or III where $R_1$ is hydrogen.

The terms "chain" or "fatty acid chain" or "fatty acid chain residue," as used with respect to the estolide compounds of Formula I, II, and III, refer to one or more of the fatty acid residues incorporated in estolide compounds, e.g., $R_3$ or $R_4$ of Formula II, or the structures represented by $CH_3(CH_2)_yCH(CH_2)_xC(O)O—$ in Formula I and III.

The $R_1$ in Formula I, II, and III at the top of each Formula shown is an example of what may be referred to as a "cap" or "capping material," as it "caps" the top of the estolide. Similarly, the capping group may be an organic acid residue of general formula —OC(O)-alkyl, i.e., a carboxylic acid with a substituted or unsubstituted, saturated or unsaturated, and/or branched or unbranched alkyl as defined herein, or a formic acid residue. In certain embodiments, the "cap" or "capping group" is a fatty acid. In certain embodiments, the capping group, regardless of size, is substituted or unsubstituted, saturated or unsaturated, and/or branched or unbranched. The cap or capping material may also be referred to as the primary or alpha (α) chain.

Depending on the manner in which the estolide is synthesized, the cap or capping group alkyl may be the only alkyl from an organic acid residue in the resulting estolide that is unsaturated. In certain embodiments, it may be desirable to use a saturated organic or fatty-acid cap to increase the overall saturation of the estolide and/or to increase the resulting estolide's stability. For example, in certain embodiments, it may be desirable to provide a method of providing a saturated capped estolide by hydrogenating an unsaturated cap using any suitable methods available to those of ordinary skill in the art. Hydrogenation may be used with various sources of the fatty-acid feedstock, which may include mono- and/or polyunsaturated fatty acids. Without being bound to any particular theory, in certain embodiments, hydrogenating the estolide may help to improve the overall stability of the molecule. However, a fully-hydrogenated estolide, such as an estolide with a larger fatty acid cap, may exhibit increased pour point temperatures. In certain embodiments, it may be desirable to offset any loss in desirable pour-point characteristics by using shorter, saturated capping materials.

The $R_4C(O)O—$ of Formula II or structure $CH_3(CH_2)_yCH(CH_2)_xC(O)O—$ of Formula I and III serve as the "base" or "base chain residue" of the estolide. Depending on the manner in which the estolide is synthesized, the base organic acid or fatty acid residue may be the only residue that remains in its free-acid form after the initial synthesis of the estolide. However, in certain embodiments, in an effort to alter or improve the properties of the estolide, the free acid may be reacted with any number of substituents. For example, it may be desirable to react the free acid estolide with alcohols, glycols, amines, or other suitable reactants to provide the corresponding ester, amide, or other reaction products. The base or base chain residue may also be referred to as tertiary or gamma (γ) chains.

The $R_3C(O)O—$ of Formula II or structure $CH_3(CH_2)_yCH(CH_2)_x(O)O—$ of Formula I and III are linking residues that link the capping material and the base fatty-acid residue together. There may be any number of linking residues in the estolide, including when n=0 and the estolide is in its dimer form. Depending on the manner in which the estolide is prepared, a linking residue may be a fatty acid and may initially be in an unsaturated form during synthesis. In some embodiments, the estolide will be formed when a catalyst is used to produce a carbocation at the fatty acid's site of unsaturation, which is followed by nucleophilic attack on the carbocation by the carboxylic group of another fatty acid. In some embodiments, it may be desirable to have a linking fatty acid that is monounsaturated so that when the fatty acids link together, all of the sites of unsaturation are eliminated. The linking residue(s) may also be referred to as secondary or beta (β) chains.

In certain embodiments, the cap is an acetyl group, the linking residue(s) is one or more fatty acid residues, and the base chain residue is a fatty acid residue. In certain embodiments, the linking residues present in an estolide differ from one another. In certain embodiments, one or more of the linking residues differs from the base chain residue.

As noted above, in certain embodiments, suitable unsaturated fatty acids for preparing the estolides may include any mono- or polyunsaturated fatty acid. For example, monounsaturated fatty acids, along with a suitable catalyst, will form a single carbocation that allows for the addition of a second fatty acid, whereby a single link between two fatty acids is formed. Suitable monounsaturated fatty acids may include, but are not limited to, palmitoleic acid (16:1), vaccenic acid (18:1), oleic acid (18:1), eicosenoic acid (20:1), erucic acid (22:1), and nervonic acid (24:1). In addition, in certain embodiments, polyunsaturated fatty acids may be used to create estolides. Suitable polyunsaturated fatty acids may include, but are not limited to, hexadecatrienoic acid (16:3), alpha-linolenic acid (18:3), stearidonic acid (18:4), eicosatrienoic acid (20:3), eicosatetraenoic acid (20:4), eicosapentaenoic acid (20:5), heneicosapentaenoic acid (21:5), docosapentaenoic acid (22:5), docosahexaenoic acid (22:6), tetracosapentaenoic acid (24:5), tetracosahexaenoic acid (24:6), linoleic acid (18:2), gamma-linoleic acid (18:3), eicosadienoic acid (20:2), dihomo-gamma-linolenic acid (20:3), arachidonic acid (20:4), docosadienoic acid (20:2), adrenic acid (22:4), docosapentaenoic acid (22:5), tetracosatetraenoic acid (22:4), tetracosapentaenoic acid (24:5), pinolenic acid (18:3), podocarpic acid (20:3), rumenic acid (18:2), alpha-calendic acid (18:3), beta-calendic acid (18:3), jacaric acid (18:3), alpha-eleostearic acid (18:3), beta-eleostearic (18:3), catalpic acid (18:3), punicic acid (18:3), rumelenic acid (18:3), alpha-parinaric acid (18:4), beta-parinaric acid (18:4), and bosseopentaenoic acid (20:5). In certain embodiments, hydroxy fatty acids may be polymerized or homopolymerized by reacting the carboxylic acid functionality of one fatty acid with the hydroxy functionality of a second fatty acid. Exemplary hydroxyl fatty acids include, but are not limited to, ricinoleic acid, 6-hydroxystearic acid, 9,10-dihydroxystearic acid, 12-hydroxystearic acid, and 14-hydroxystearic acid.

The process for preparing the estolide compounds described herein may include the use of any natural or synthetic fatty acid source. However, it may be desirable to source the fatty acids from a renewable biological feedstock. For example, suitable starting materials of biological origin include, but are not limited to, plant fats, plant oils, plant waxes, animal fats, animal oils, animal waxes, fish fats, fish oils, fish waxes, algal oils and mixtures of two or more thereof. Other potential fatty acid sources include, but are not limited to, waste and recycled food-grade fats and oils, fats, oils, and waxes obtained by genetic engineering, fossil fuel-based materials and other sources of the materials desired.

In some embodiments, the compound comprises chain residues of varying lengths. In some embodiments, x is, independently for each occurrence, an integer selected from 0 to 20, 0 to 18, 0 to 16, 0 to 14, 1 to 12, 1 to 10, 2 to 8, 6 to 8, or 4 to 6. In some embodiments, x is, independently for each occurrence, an integer selected from 7 and 8. In some embodiments, x is, independently for each occurrence, an integer selected from 0, 1, 2, 3, 4, 5, 6, 7, 8, 9, 10, 11, 12, 13, 14, 15, 16, 17, 18, 19, and 20. In certain embodiments, for at least one chain residue, x is an integer selected from 7 and 8.

In some embodiments, y is, independently for each occurrence, an integer selected from 0 to 20, 0 to 18, 0 to 16, 0 to 14, 1 to 12, 1 to 10, 2 to 8, 6 to 8, or 4 to 6. In some embodiments, y is, independently for each occurrence, an integer selected from 7 and 8. In some embodiments, y is, independently for each occurrence, an integer selected from 0, 1, 2, 3, 4, 5, 6, 7, 8, 9, 10, 11, 12, 13, 14, 15, 16, 17, 18, 19, and 20. In certain embodiments, for at least one chain residue, y is an integer selected from 7 and 8. In some embodiments, for at least one chain residue, y is an integer selected from 0 to 6, or 1 and 2. In certain embodiments, y is, independently for each occurrence, an integer selected from 1 to 6, or 1 and 2.

In some embodiments, x+y is, independently for each chain, an integer selected from 0 to 40, 0 to 20, 10 to 20, or 12 to 18. In some embodiments, x+y is, independently for each chain, an integer selected from 13 to 15. In some embodiments, x+y is 15. In some embodiments, x+y is, independently for each chain, an integer selected from 6, 7, 8, 9, 10, 11, 12, 13, 14, 15, 16, 17, 18, 19, 20, 21, 22, 23, and 24.

In some embodiments, the estolide compound of Formula I, II, or III may comprise any number of fatty acid residues to form an "n-mer" estolide. For example, the estolide may be in its dimer (n=0), trimer (n=1), tetramer (n=2), pentamer (n=3), hexamer (n=4), heptamer (n=5), octamer (n=6), nonamer (n=7), or decamer (n=8) form. In some embodiments, n is an integer selected from 0 to 20, 0 to 18, 0 to 16, 0 to 14, 0 to 12, 0 to 10, 0 to 8, or 0 to 6. In some embodiments, n is an integer selected from 0 to 4. In some embodiments, n is 0 or greater than 0. In some embodiments, n is 1, wherein said at least one compound of Formula I, II, or III comprises the trimer. In some embodiments, n is greater than 1. In some embodiments, n is an integer selected from 0, 1, 2, 3, 4, 5, 6, 7, 8, 9, 10, 11, 12, 13, 14, 15, 16, 17, 18, 19, and 20.

In some embodiments, $R_1$ of Formula I, II, or III is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_1$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_1$ is selected from $C_{13}$ to $C_{17}$ alkyl, such as from $C_{13}$ alkyl, $C_{15}$ alkyl, and $C_{17}$ alkyl. In some embodiments, $R_1$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_2$ of Formula I, II, or III is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_2$ is selected from $C_7$ alkyl, $C_9$ alkyl, $C_{1i}$ alkyl, $C_{13}$ alkyl, $C_{15}$ alkyl, and $C_{17}$ alkyl. In some embodiments, $R_2$ is selected from $C_{13}$ to $C_{17}$ alkyl, such as from $C_{13}$ alkyl, $C_{15}$ alkyl, and $C_{17}$ alkyl. In some embodiments, $R_2$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_3$ is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_3$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_3$ is selected from $C_{13}$ to $C_{17}$ alkyl, such as from $C_{13}$ alkyl, $C_{15}$ alkyl, and $C_{17}$ alkyl. In some embodiments, $R_3$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_4$ is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_4$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_4$ is selected from $C_{13}$ to $C_{17}$ alkyl, such as from $C_{13}$ alkyl, $C_{15}$ alkyl, and $C_{17}$ alkyl. In some embodiments, $R_4$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

As noted above, in certain embodiments, it may be possible to manipulate one or more of the estolides' properties by altering the length of $R_1$ and/or its degree of saturation. However, in certain embodiments, the level of substitution on $R_1$ may also be altered to change or even improve the estolides' properties. Without being bound to any particular theory, in certain embodiments, it is believed that the presence of polar substituents on $R_1$, such as one or more hydroxy groups, may increase the viscosity of the estolide, while increasing pour point. Accordingly, in some embodiments, $R_1$ will be unsubstituted or optionally substituted with a group that is not hydroxyl.

In some embodiments, the estolide is in its free-acid form, wherein $R_2$ of Formula I, II, or III is hydrogen. In some embodiments, $R_2$ is selected from optionally substituted alkyl that is saturated or unsaturated, and branched or unbranched. In certain embodiments, the $R_2$ residue may comprise any desired alkyl group, such as those derived from esterification of the estolide with the alcohols identified in the examples herein. In some embodiments, the alkyl group is selected from $C_1$ to $C_{40}$, $C_1$ to $C_{22}$, $C_3$ to $C_{20}$, $C_1$ to $C_{18}$, or $C_6$ to $C_{12}$ alkyl. In some embodiments, $R_2$ may be selected from $C_3$ alkyl, $C_4$ alkyl, $C_8$ alkyl, $C_{12}$ alkyl, $C_{16}$ alkyl, $C_{18}$ alkyl, and $C_{20}$ alkyl. For example, in certain embodiments, $R_2$ may be branched, such as isopropyl, isobutyl, or 2-ethylhexyl. In some embodiments, $R_2$ may be a larger alkyl group, branched or unbranched, comprising $C_{12}$ alkyl, $C_{16}$ alkyl, $C_{18}$ alkyl, or $C_{20}$ alkyl. Such groups at the $R_2$ position may be derived from esterification of the free-acid estolide using the Jarcol™ line of alcohols marketed by Jarchem Industries, Inc. of Newark, N.J., including Jarcol™ I-18CG, I-20, I-12, I-16, I-18T, and 85BJ. In some cases, $R_2$ may be sourced from certain alcohols to provide branched alkyls such as isostearyl and isopalmityl. It should be understood that such isopalmityl and isostearyl alkyl groups may cover any branched variation of $C_{16}$ and $C_{18}$, respectively. For example, the estolides described herein may comprise highly-branched isopalmityl or isostearyl groups at the $R_2$ position, derived from the Fineoxocol® line of isopalmityl and isostearyl alcohols marketed by Nissan Chemical America Corporation of Houston, Tex., including Fineoxocol®180, 180N, and 1600. Without being bound to any particular theory, in certain embodiments, large, highly-branched alkyl groups (e.g., isopalmityl and isostearyl) at the $R_2$ position of the estolides can provide at least one way to increase an estolide-containing composition's viscosity, while substantially retaining or even reducing its pour point.

In some embodiments, the compounds described herein may comprise a mixture of two or more estolide compounds of Formula I, II, and III. It is possible to characterize the chemical makeup of an estolide, a mixture of estolides, or a composition comprising estolides, by using the compound's, mixture's, or composition's measured estolide number (EN) of compound or composition. The EN represents the average number of fatty acids added to the base fatty acid. The EN also represents the average number of estolide linkages per molecule:

EN=$n$+1 wherein n is the number of secondary (β) fatty acids. Accordingly, a single estolide compound will have an EN that is a whole number, for example for dimers, trimers, and tetramers:

dimer EN=1 trimer EN=2 tetramer EN=3

However, a composition comprising two or more estolide compounds may have an EN that is a whole number or a fraction of a whole number. For example, a composition having a 1:1 molar ratio of dimer and trimer would have an EN of 1.5, while a composition having a 1:1 molar ratio of tetramer and trimer would have an EN of 2.5.

In some embodiments, the compositions may comprise a mixture of two or more estolides having an EN that is an integer or fraction of an integer that is greater than 4.5, or even 5.0. In some embodiments, the EN may be an integer or fraction of an integer selected from about 1.0 to about 5.0. In some embodiments, the EN is an integer or fraction of an integer selected from 1.2 to about 4.5. In some embodiments, the EN is selected from a value greater than 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6 and 5.8. In some embodiments, the EN is selected from a value less than 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, and 5.0, 5.2, 5.4, 5.6, 5.8, and 6.0. In some embodiments, the EN is selected from 1, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, and 6.0.

As noted above, it should be understood that the chains of the estolide compounds may be independently optionally substituted, wherein one or more hydrogens are removed and replaced with one or more of the substituents identified herein. Similarly, two or more of the hydrogen residues may be removed to provide one or more sites of unsaturation, such as a cis or trans double bond. Further, the chains may optionally comprise branched hydrocarbon residues. For example, in some embodiments the estolides described herein may comprise at least one compound of Formula II:

Formula II

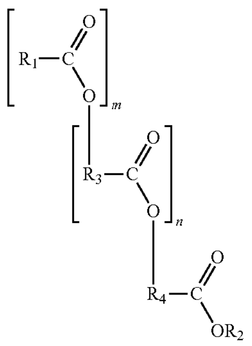

wherein m is an integer equal to or greater than 1;

n is an integer equal to or greater than 0;

$R_1$, independently for each occurrence, is an optionally substituted alkyl that is saturated or unsaturated, and branched or unbranched;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched.

In certain embodiments, m is 1. In some embodiments, m is an integer selected from 2, 3, 4, and 5. In some embodiments, n is an integer selected from 1, 2, 3, 4, 5, 6, 7, 8, 9, 10, 11, and 12. In some embodiments, one or more $R_3$ differs from one or more other $R_3$ in a compound of Formula II. In some embodiments, one or more $R_3$ differs from $R_4$ in a compound of Formula II. In some embodiments, if the compounds of Formula II are prepared from one or more polyunsaturated fatty acids, it is possible that one or more of $R_3$ and $R_4$ will have one or more sites of unsaturation. In some embodiments, if the compounds of Formula II are prepared from one or more branched fatty acids, it is possible that one or more of $R_3$ and $R_4$ will be branched.

In some embodiments, $R_3$ and $R_4$ can be $CH_3(CH_2)_yCH(CH_2)_x$—, where x is, independently for each occurrence, an integer selected from 0, 1, 2, 3, 4, 5, 6, 7, 8, 9, 10, 11, 12, 13, 14, 15, 16, 17, 18, 19, and 20, and y is, independently for each occurrence, an integer selected from 0, 1, 2, 3, 4, 5, 6, 7, 8, 9, 10, 11, 12, 13, 14, 15, 16, 17, 18, 19, and 20. Where both $R_3$ and $R_4$ are $CH_3(CH_2)_yCH(CH_2)_x$—, the compounds may be compounds according to Formula I and III.

Without being bound to any particular theory, in certain embodiments, altering the EN produces estolide-containing compositions having desired viscometric properties while substantially retaining or even reducing pour point. For example, in some embodiments the estolides exhibit a decreased pour point upon increasing the EN value. Accordingly, in certain embodiments, a method is provided for retaining or decreasing the pour point of an estolide base oil by increasing the EN of the base oil, or a method is provided for retaining or decreasing the pour point of a composition comprising an estolide base oil by increasing the EN of the base oil. In some embodiments, the method comprises: selecting an estolide base oil having an initial EN and an initial pour point; and removing at least a portion of the base oil, said portion exhibiting an EN that is less than the initial EN of the base oil, wherein the resulting estolide base oil exhibits an EN that is greater than the initial EN of the base oil, and a pour point that is equal to or lower than the initial pour point of the base oil. In some embodiments, the selected estolide base oil is prepared by oligomerizing at least one first unsaturated fatty acid with at least one second unsaturated fatty acid and/or saturated fatty acid. In some embodiments, the removing at least a portion of the base oil or a composition comprising two or more estolide compounds is accomplished by use of at least one of distillation, chromatography, membrane separation, phase separation, affinity separation, and solvent extraction. In some embodiments, the distillation takes place at a temperature and/or pressure that is suitable to separate the estolide base oil or a composition comprising two or more estolide compounds into different "cuts" that individually exhibit different EN values. In some embodiments, this may be accomplished by subjecting the base oil or a composition comprising two or more estolide compounds to a temperature of at least about 250° C. and an absolute pressure of no greater than about 25 microns. In some embodiments, the distillation takes place at a temperature range of about 250° C. to about 310° C. and an absolute pressure range of about 10 microns to about 25 microns.

In some embodiments, estolide compounds and compositions exhibit an EN that is greater than or equal to 1, such as an integer or fraction of an integer selected from about 1.0 to about 2.0. In some embodiments, the EN is an integer or fraction of an integer selected from about 1.0 to about 1.6. In some embodiments, the EN is a fraction of an integer selected from about 1.1 to about 1.5. In some embodiments, the EN is selected from a value greater than 1.0, 1.1, 1.2, 1.3, 1.4, 1.5, 1.6, 1.7, 1.8, and 1.9. In some embodiments, the EN is selected from a value less than 1.1, 1.2, 1.3, 1.4, 1.5, 1.6, 1.7, 1.8, 1.9, and 2.0.

In some embodiments, the EN is greater than or equal to 1.5, such as an integer or fraction of an integer selected from about 1.8 to about 2.8. In some embodiments, the EN is an integer or fraction of an integer selected from about 2.0 to about 2.6. In some embodiments, the EN is a fraction of an integer selected from about 2.1 to about 2.5. In some embodiments, the EN is selected from a value greater than 1.8, 1.9, 2.0, 2.1, 2.2, 2.3, 2.4, 2.5, 2.6, and 2.7. In some embodiments, the EN is selected from a value less than 1.9, 2.0, 2.1, 2.2, 2.3, 2.4, 2.5, 2.6, 2.7, and 2.8. In some embodiments, the EN is about 1.8, 2.0, 2.2, 2.4, 2.6, or 2.8.

In some embodiments, the EN is greater than or equal to about 4, such as an integer or fraction of an integer selected from about 4.0 to about 5.0. In some embodiments, the EN is a fraction of an integer selected from about 4.2 to about 4.8. In some embodiments, the EN is a fraction of an integer selected from about 4.3 to about 4.7. In some embodiments, the EN is selected from a value greater than 4.0, 4.1, 4.2, 4.3, 4.4, 4.5, 4.6, 4.7, 4.8, and 4.9. In some embodiments, the EN is selected from a value less than 4.1, 4.2, 4.3, 4.4, 4.5, 4.6, 4.7, 4.8, 4.9, and 5.0. In some embodiments, the EN is about 4.0, 4.2, 4.4, 4.6, 4.8, or 5.0.

In some embodiments, the EN is greater than or equal to about 5, such as an integer or fraction of an integer selected from about 5.0 to about 6.0. In some embodiments, the EN is a fraction of an integer selected from about 5.2 to about 5.8. In some embodiments, the EN is a fraction of an integer selected from about 5.3 to about 5.7. In some embodiments, the EN is selected from a value greater than 5.0, 5.1, 5.2, 5.3, 5.4, 5.5, 5.6, 5.7, 5.8, and 5.9. In some embodiments, the EN is selected from a value less than 5.1, 5.2, 5.3, 5.4, 5.5, 5.6, 5.7, 5.8, 5.9, and 6.0. In some embodiments, the EN is about 5.0, 5.2, 5.4, 5.4, 5.6, 5.8, or 6.0.

In some embodiments, the EN is greater than or equal to 1, such as an integer or fraction of an integer selected from about 1.0 to about 2.0. In some embodiments, the EN is a fraction of an integer selected from about 1.1 to about 1.7. In some embodiments, the EN is a fraction of an integer selected from about 1.1 to about 1.5. In some embodiments, the EN is selected from a value greater than 1.0, 1.1, 1.2, 1.3, 1.4, 1.5, 1.6, 1.7, 1.8, or 1.9. In some embodiments, the EN is selected from a value less than 1.2, 1.3, 1.4, 1.5, 1.6, 1.7, 1.8, 1.9, or 2.0. In some embodiments, the EN is about 1.0, 1.2, 1.4, 1.6, 1.8, or 2.0. In some embodiments, the EN is greater than or equal to 1, such as an integer or fraction of an integer selected from about 1.2 to about 2.2. In some embodiments, the EN is an integer or fraction of an integer selected from about 1.4 to about 2.0. In some embodiments, the EN is a fraction of an integer selected from about 1.5 to about 1.9. In some embodiments, the EN is selected from a value greater than 1.0, 1.1, 1.2, 1.3, 1.4, 1.5, 1.6, 1.7, 1.8, 1.9, 2.0, and 2.1. In some embodiments, the EN is selected from a value less than 1.2, 1.3, 1.4, 1.5, 1.6, 1.7, 1.8, 1.9, 2.0, 2.1, and 2.2. In some embodiments, the EN is about 1.0, 1.2, 1.4, 1.6, 1.8, 2.0, or 2.2.

In some embodiments, the EN is greater than or equal to 2, such as an integer or fraction of an integer selected from about 2.8 to about 3.8. In some embodiments, the EN is an integer or fraction of an integer selected from about 2.9 to about 3.5. In some embodiments, the EN is an integer or fraction of an integer selected from about 3.0 to about 3.4. In some embodiments, the EN is selected from a value greater than 2.0, 2.1, 2.2., 2.4, 2.5, 2.6, 2.7, 2.8, 2.9, 3.0, 3.1, 3.4, 3.5, 3.6, and 3.7. In some embodiments, the EN is selected from a value less than 2.2, 2.3, 2.4, 2.5, 2.6, 2.7, 2.8, 2.9, 3.0, 3.1, 3.2, 3.3, 3.4, 3.5, 3.6, 3.7, and 3.8. In some embodiments, the EN is about 2.0, 2.2, 2.4, 2.6, 2.8, 3.0, 3.2, 3.4, 3.6, or 3.8.

Typically, base stocks and estolide-containing compositions exhibit certain lubricity, viscosity, and/or pour point characteristics. For example, in certain embodiments, the base oils, compounds, and compositions may exhibit viscosities that range from about 10 cSt to about 250 cSt at 40° C., and/or about 3 cSt to about 30 cSt at 100° C. In some embodiments, the base oils, compounds, and compositions may exhibit viscosities within a range from about 50 cSt to about 150 cSt at 40° C., and/or about 10 cSt to about 20 cSt at 100° C.

In some embodiments, the estolide compounds and compositions may exhibit viscosities less than about 55 cSt at 40° C. or less than about 45 cSt at 40° C., and/or less than about 12 cSt at 100° C. or less than about 10 cSt at 100° C. In some embodiments, the estolide compounds and compositions may exhibit viscosities within a range from about 25 cSt to about 55 cSt at 40° C., and/or about 5 cSt to about 11 cSt at 100° C. In some embodiments, the estolide compounds and compositions may exhibit viscosities within a range from about 35 cSt to about 45 cSt at 40° C., and/or about 6 cSt to about 10 cSt at 100° C. In some embodiments, the estolide compounds and compositions may exhibit viscosities within a range from about 38 cSt to about 43 cSt at 40° C., and/or about 7 cSt to about 9 cSt at 100° C.

In some embodiments, the estolide compounds and compositions may exhibit viscosities less than about 120 cSt at 40° C. or less than about 100 cSt at 40° C., and/or less than about 18 cSt at 100° C. or less than about 17 cSt at 100° C. In some embodiments, the estolide compounds and compositions may exhibit a viscosity within a range from about 70 cSt to about 120 cSt at 40° C., and/or about 12 cSt to about 18 cSt at 100° C. In some embodiments, the estolide compounds and compositions may exhibit viscosities within a range from about 80 cSt to about 100 cSt at 40° C., and/or about 13 cSt to about 17 cSt at 100° C. In some embodiments, the estolide compounds and compositions may exhibit viscosities within a range from about 85 cSt to about 95 cSt at 40° C., and/or about 14 cSt to about 16 cSt at 100° C.

In some embodiments, the estolide compounds and compositions may exhibit viscosities greater than about 180 cSt at 40° C. or greater than about 200 cSt at 40° C., and/or greater than about 20 cSt at 100° C. or greater than about 25 cSt at 100° C. In some embodiments, the estolide compounds and compositions may exhibit a viscosity within a range from about 180 cSt to about 230 cSt at 40° C., and/or about 25 cSt to about 31 cSt at 100° C. In some embodiments, the estolide compounds and compositions may exhibit viscosities within a range from about 200 cSt to about 250 cSt at 40° C., and/or about 25 cSt to about 35 cSt at 100° C. In some embodiments, the estolide compounds and compositions may exhibit viscosities within a range from about 210 cSt to about 230 cSt at 40° C., and/or about 28 cSt to about 33 cSt at 100° C. In some embodiments, the estolide compounds and compositions may exhibit viscosities within a range from about 200 cSt to about 220 cSt at 40° C., and/or about 26 cSt to about 30 cSt at 100° C. In some embodiments, the estolide compounds and compositions may exhibit viscosities within a range from about 205 cSt to about 215 cSt at 40° C., and/or about 27 cSt to about 29 cSt at 100° C.

In some embodiments, the estolide compounds and compositions may exhibit viscosities less than about 45 cSt at 40° C. or less than about 38 cSt at 40° C., and/or less than about 10 cSt at 100° C. or less than about 9 cSt at 100° C. In some embodiments, the estolide compounds and compositions may exhibit a viscosity within a range from about 20 cSt to about 45 cSt at 40° C., and/or about 4 cSt to about 10 cSt at 100° C. In some embodiments, the estolide compounds and compositions may exhibit viscosities within a range from about 28 cSt to about 38 cSt at 40° C., and/or about 5 cSt to about 9 cSt at 100° C. In some embodiments, the estolide compounds and compositions may exhibit viscosities within a range from about 30 cSt to about 35 cSt at 40° C., and/or about 6 cSt to about 8 cSt at 100° C.

In some embodiments, the estolide compounds and compositions may exhibit viscosities less than about 80 cSt at 40° C. or less than about 70 cSt at 40° C., and/or less than about 14 cSt at 100° C. or less than about 13 cSt at 100° C. In some embodiments, the estolide compounds and compositions may exhibit a viscosity within a range from about 50 cSt to about 80 cSt at 40° C., and/or about 8 cSt to about 14 cSt at 100° C. In some embodiments, the estolide compounds and compositions may exhibit viscosities within a range from about 60 cSt to about 70 cSt at 40° C., and/or about 9 cSt to about 13 cSt at 100° C. In some embodiments, the estolide compounds and compositions may exhibit viscosities within a range from about 63 cSt to about 68 cSt at 40° C., and/or about 10 cSt to about 12 cSt at 100° C.

In some embodiments, the estolide compounds and compositions may exhibit viscosities greater than about 120 cSt at 40° C. or greater than about 130 cSt at 40° C., and/or greater than about 15 cSt at 100° C. or greater than about 18 cSt at 100° C. In some embodiments, the estolide compounds and compositions may exhibit a viscosity within a range from about 120 cSt to about 150 cSt at 40° C., and/or about 16 cSt to about 24 cSt at 100° C. In some embodiments, the estolide compounds and compositions may exhibit viscosities within a range from about 130 cSt to about 160 cSt at 40° C., and/or about 17 cSt to about 28 cSt at 100° C. In some embodiments, the estolide compounds and compositions may exhibit viscosities within a range from about 130 cSt to about 145 cSt at 40° C., and/or about 17 cSt to about 23 cSt at 100° C. In some embodiments, the estolide compounds and compositions may exhibit viscosities within a range from about 135 cSt to about 140 cSt at 40° C., and/or about 19 cSt to about 21 cSt at 100° C. In some embodiments, the estolide compounds and compositions may exhibit viscosities of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, or 400 cSt. at 40° C. In some embodiments, the estolide compounds and compositions may exhibit viscosities of about 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 cSt at 100° C.

In some embodiments, the estolide compounds and compositions may exhibit viscosities less than about 200, 250, 300, 350, 400, 450, 500, or 550 cSt at 0° C. In some embodiments, the estolide compounds and compositions may exhibit a viscosity within a range from about 200 cSt to about 250 cSt at 0° C. In some embodiments, the estolide compounds and compositions may exhibit a viscosity within a range from about 250 cSt to about 300 cSt at 0° C. In some embodiments, the estolide compounds and compositions may exhibit a viscosity within a range from about 300 cSt to about 350 cSt at 0° C. In some embodiments, the estolide compounds and compositions may exhibit a viscosity within a range from about 350 cSt to about 400 cSt at 0° C. In some embodiments, the estolide compounds and compositions may exhibit a viscosity within a range from about 400 cSt to about 450 cSt at 0° C. In some embodiments, the estolide compounds and compositions may exhibit a viscosity within a range from about 450 cSt to about 500 cSt at 0° C. In some embodiments, the estolide compounds and compositions may exhibit a viscosity within a range from about 500 cSt to about 550 cSt at 0° C. In some embodiments, the estolide compounds and compositions may exhibit viscosities of about 100, 125, 150, 175, 200, 225, 250, 275, 300, 325, 350, 375, 400, 425, 450, 475, 500, 525, or 550 cSt at 0° C.

In some embodiments, estolide compounds and compositions may exhibit desirable low-temperature pour point properties. In some embodiments, the estolide compounds and compositions may exhibit a pour point lower than about −20° C., about −25° C., about −35° C., −40° C., or even about −50° C. In some embodiments, the estolide compounds and compositions have a pour point of about −25° C. to about −45° C. In some embodiments, the pour point falls within a range of about −30° C. to about −40° C., about −34° C. to about −38° C., about −30° C. to about −45° C., −35° C. to about −45° C., 34° C. to about −42° C., about −38° C. to about −42° C., or about 36° C. to about −40° C. In some embodiments, the pour point falls within the range of about −27° C. to about −37° C., or about −30° C. to about −34° C. In some embodiments, the pour point falls within the range of about −25° C. to about −35° C., or about −28° C. to about −32° C. In some embodiments, the pour point falls within the range of about −28° C. to about −38° C., or about −31° C. to about −35° C. In some embodiments, the pour point falls within the range of about −31° C. to about −41° C., or about −34° C. to about −38° C. In some embodiments, the pour point falls within the range of about −40° C. to about −50° C., or about −42° C. to about −48° C. In some embodiments, the pour point falls within the range of about −50° C. to about −60° C., or about −52° C. to about −58° C. In some embodiments, the upper bound of the pour point is less than about −35° C., about −36° C., about −37° C., about −38° C., about −39° C., about −40° C., about −41° C., about −42° C., about −43° C., about −44° C., or about −45° C. In some embodiments, the lower bound of the pour point is greater than about −70° C., about −69° C., about −68° C., about −67° C., about −66° C., about −65° C., about −64° C., about −63° C., about −62° C., about −61° C., about −60° C., about −59° C., about −58° C., about −57° C., about −56° C., −55° C., about −54° C., about −53° C., about −52° C., −51, about −50° C., about −49° C., about −48° C., about −47° C., about −46° C., or about −45° C.

In addition, in certain embodiments, the estolides may exhibit decreased Iodine Values (IV) when compared to estolides prepared by other methods. IV is a measure of the degree of total unsaturation of an oil, and is determined by measuring the amount of iodine per gram of estolide (cg/g). In certain instances, oils having a higher degree of unsaturation may be more susceptible to creating corrosiveness and deposits, and may exhibit lower levels of oxidative stability. Compounds having a higher degree of unsaturation will have more points of unsaturation for iodine to react with, resulting in a higher IV. Thus, in certain embodiments, it may be desirable to reduce the IV of estolides in an effort to increase the oil's oxidative stability, while also decreasing harmful deposits and the corrosiveness of the oil.

In some embodiments, estolide compounds and compositions described herein have an IV of less than about 40 cg/g or less than about 35 cg/g. In some embodiments, estolides have an IV of less than about 30 cg/g, less than about 25 cg/g, less than about 20 cg/g, less than about 15 cg/g, less than about 10 cg/g, or less than about 5 cg/g. In some embodiments, estolides have an IV of about 0 cg/g. The IV of a composition may be reduced by decreasing the estolide's degree of unsaturation. This may be accomplished by, for example, by increasing the amount of saturated capping materials relative to unsaturated capping materials when synthesizing the estolides. Alternatively, in certain embodiments, IV may be reduced by hydrogenating estolides having unsaturated caps.

In certain embodiments, the composition is a lubricating composition. In certain embodiments, the composition comprises an estolide base oil, wherein the estolide base oil comprises at least one estolide compound. In certain embodiments, the composition comprises a combination of an estolide base oil and at least one antioxidant. Unless noted otherwise, an indication of the characteristics of the "combination" of an estolide base oil and at least one antioxidant refers specifically to the properties of a mixture of the estolide base oil and the at least one antioxidant, absent any other components that may be present in the overall composition. In certain embodiments, one or more properties of the composition will be similar to, or substantially the same as, the properties of the combination of the estolide base oil and the at least one antioxidant.

In certain embodiments, the composition has a kinematic viscosity essentially the same as the kinematic viscosity for the estolide base oil included in the composition. In certain embodiments, the composition has a kinematic viscosity within approximately 1% or approximately 2% of the kinematic viscosity of the estolide base oil included within the composition. In certain embodiments, the composition has a kinematic viscosity within 0.2%, 0.4%, 0.6%, 0.8%, 1.0%, 1.2%, 1.4%, 1.6%, 1.8%, or 2% of the kinematic viscosity of the estolide estolide base oil included in the composition. In certain embodiments, the composition has a kinematic viscosity that is less than or equal to about 15 cSt at 100° C. In certain embodiments, the composition has a kinematic viscosity that is less than or equal to about 50 cSt at 40° C. In certain embodiments, the composition has a kinematic viscosity that is less than or equal to about 500 cSt at 0° C.

In certain embodiments, the estolide base oil has a total acid number equal to or less than about 0.5, 0.4, 0.3, 0.2, or even 0.1 mg KOH/g. In certain embodiments, the estolide base oil has a total acid number of less than about 0.1 mg KOH/g, such as about 0.05 to about 0.1 mg KOH/g. In certain embodiments, the estolide base oil has a total acid number equal to or less than about 0.05 mg KOH/g. In certain embodiments, the estolide base oil has a total acid number of about 0.02 to about 0.06 mg KOH/g. In certain embodiments, the estolide base oil has a total acid number of about 0, 0.01, 0.02, 0.03, 0.04, 0.05, 0.06, 0.07, 0.08, 0.09, or 0.1 mg KOH/g. In certain embodiments, the composition has a total acid number essentially the same as the total acid number for the estolide base oil included in the composition.

In certain embodiments, the compositions described herein comprise or consist essentially of an estolide base oil, wherein said base oil comprises at least one compound of Formulas I, II, and/or III. In certain embodiments, the composition further comprises at least one additive, wherein the at least one additive may be selected from one or more of an antioxidant, an antimicrobial agent, an extreme pressure agent, a friction modifier, a pour point depressant, a metal chelating agent, a metal deactivator, an antifoaming agent, or a demulsifier. In certain embodiments, the composition comprises or consists essentially of an estolide base oil and at least one antioxidant. In certain embodiments, the composition further comprises at least one lubricating oil. In certain embodiments, the lubricating oil is not an estolide base oil. In certain embodiments, the lubricating oil is selected from a Group I oil, a Group II oil, a Group III oil, a polyalphaolefin, a polyol ester, a polyalkylene glycol, and an oil soluble polyalkylene glycol.

In certain embodiments, the composition comprises or consists essentially of a combination of an estolide base oil and at least one additive. In certain embodiments, the at least one additive is an antioxidant. In certain embodiments, the at least one antioxidant is selected from phenolic antioxidants, amine antioxidants, and organometallic antioxidants. In certain embodiments, the at least one antioxidant is a phenolic antioxidant. In certain embodiments, the at least one antioxidant is a hindered phenolic antioxidant. In certain embodiments, the at least one antioxidant is an amine antioxidant, such as a diarylamine, benzylamine, or polyamine. In certain embodiments, the at least one antioxidant is a diarylamine antioxidant, such as an alkylated diphenylamine antioxidant. In certain embodiments, the at least one antioxidant is a phenyl-α-naphthylamine or an alkylated phenyl-α-naphthylamine. In certain embodiments, the at least one antioxidant comprises an antioxidant package. In certain embodiments, the antioxidant package comprises one or more phenolic antioxidants and one or more amine antioxidants, such as a combination of a hindered phenolic antioxidant and an alkylated diphenylamine antioxidant. Exemplary antioxidants include, but are not limited to, zinc dithiophosphates (ZDDP), butylated hydroxy anisole (BHA), 2,6-ditertiary-butyl paracresol (DBPC), mono-tertiary butyl hydro quinone (TBHQ), tetrahydro butyrophenone (THBP), hydroquinone, pyrogallol, propyl gallate, phenothiazine, and one or more tocopherols. Other exemplary antioxidants include, but are not limited to, hydroxylamines, amine N-oxides, oximes, and nitrones. In certain embodiments, the at least one antioxidant is dithiocarbamate. In certain embodiments, the dithiocarbamate is a metal dialkyl dithiocarbamate, such as, for example, zinc diamyl dithiocarbamate (ZDDC). In certain embodiments, zinc diamyl dithiocarbamate may have a synergistic effect with one or more extreme pressure agents, such as antimony dialkyl dithiocarbamate (ADDC).

In certain embodiments, the at least one antioxidant is an amine antioxidant. In certain embodiments, the at least one antioxidant is an alkylated diphenylamine selected from a nonylated diphenylamine and an octylated/butylated diphenylamine. In certain embodiments, the at least one antioxidant is selected from N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N-bis(2-naphthyl) -p-phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylamino methylphenol, 2,4'-diaminodiphenylmethane, 4,4'-diaminodiphenylmethane, N,N,N',N'-tetramethyl-4,4'-diaminodiphenylmethane, 1,2-bis[(2-methyl-phenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, mono- and dialkylated tert-butyl/tert-octyldiphenylamines, mono- and dialkylated isopropyl/isohexyldiphenylamines, mono- and dialkylated tert-butyldiphenylamines, mono- and dialkylated nonyl diphenylamines, mono- and dialkylated octyl/butyldiphenylamines, 2,3-dihydro-3,3-dimethyl-4H-1,4-benzothiazine, phenothiazine, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethyl piperid-4-yl)sebacate, 2,2,6,6-tetramethylpiperidin-4-one and 2,2,6,6-tetramethyl piperidin-4-ol.

In certain embodiments, the at least one antioxidant is an alkylated monophenol. In certain embodiments, the at least one antioxidant is an alkylated diphenol. In certain embodiments, the at least one antioxidant is an alkylidene bisphenol. In certain embodiments, the at least one antioxidant is selected from 2,6-di-tert-butylphenol, 4,4'-methylene-bis(2,6-di-tert-butylphenol), 4,4'-bis(2,6-di-tert-butylphenol), 4,4'-bis(2-methyl-6-tert-butylphenol), 2,2'-methylene-bis(4-methyl-6-tert-butylphenol), 4,4'-butylidene-bis(3-methyl-6-tert-butylphenol), 4,4'-isopropylidene-bis(2,6-di-tert-butylphenol), 2,2'-methylene-bis(4-methyl-6-nonylphenol), 2,2'-isobutylidene-bis(4,6-dimethylphenol), 2,2'-methylene-bis(4-methyl-6-cyclohexylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercapto butane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl] terephthalate, 1,1-bis-(3,5-dimethyl-2-hydroxyphenyl) butane, 2,2-bis-(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra-(5-tert-butyl-4-hydroxy-2-methyl phenyl)pentane, 2,6-di-tert-butyl-4-methylphenol (butylated hydroxytoluene (BHT)), 2,6-di-tert-butyl-4-ethylphenol, 2,4-dimethyl-6-tert-butyl-phenol, 2,6-di-tert-butyl-N,N'-dimethylamino-p-cresol, 2,6-di-tert-4-(N,N'-dimethylaminomethylphenol), heptyl 3-(3',5'-di-butyl-4'-hydroxyphenyl)propionate, octyl 3-(3',5'-di-butyl-4'-hydroxyphenyl)propionate, nonyl 3-(3',5'-di-butyl-4'-hydroxyphenyl)propionate, octadecyl 3-(3',5'-di-butyl-4'-hydroxyphenyl)propionate, 2-tert-butyl-4,6-dimethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6(1'-methylundec-1'-yl)phenol, 2,4-dimethyl-6-(1'-methylheptadec-1'-yl)phenol, and 2,4-dimethyl-6-(1'-methyltridec-1'-yl)phenol.

In certain embodiments, the at least one antioxidant is selected from an alkylthiomethylphenol and a hydroxylated thiodiphenyl ether. In certain embodiments, the at least one antioxidant is selected from 4,4'-thiobis(2-methyl-6-tert-butylphenol), 2,2'-thiobis(4-methyl-6-tert-butylphenol), bis(3-methyl-4-hydroxy-5-tert-butylbenzyl) -sulfide, thiodiethylene-bis-(3,5-di-t-butyl-4-hydroxyhydrocinnamate), tetrakis-(methylene-(3,5-di-t-butyl-4-hydrocinnamate))methane, bis (3,5-di-tert-butyl-4-hydroxybenzyl)-sulfide, 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol, 2,2'-thiobis(4-octylphenol), 4,4'-thiobis(6-tert-butyl-3-methylphenol), 4,4'-thiobis-(3,6-di-sec-amylphenol), and 4,4'-bis-(2,6-dimethyl-4-hydroxyphenyl)disulfide.

In certain embodiments, the at least one antioxidant is selected from hydroquinones and alkylated hydroquinones. In certain embodiments, the at least one antioxidant is selected from 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, and bis-(3,5-di-tert-butyl-4-hydroxyphenyl)adipate.

In certain embodiments, the at least one antioxidant is selected from O-, N- and S-benzyl compounds. In certain embodiments, the at least one antioxidant is selected from 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithiol terephthalate, bis(3,5-di-tert-butyl-4-hydroxybenzyl)sulfide, and isooctyl-3,5di-tert-butyl-4-hydroxy benzylmercaptoacetate.

In certain embodiments, the at least one antioxidant is selected from hydroxybenzylated malonates. In certain embodiments, the at least one antioxidant is selected from dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, and bis[4-(1,1,3,3-tetramethylbutyl)phenyl]-2,2-bis(3,5-di-tert-butyl-4-hydroxybenzyl)malonate.

In certain embodiments, the at least one antioxidant is selected from triazine compounds. In certain embodiments, the at least one antioxidant is selected from 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl 2,4,6-tris(3,5-di-tert-butyl-4-hydroxyphenylethyl)-1,3,5-triazine, 1,3,5-tris(3,5-di-tert-butyl-4-hydroxyphenyl propionyl)-hexahydro-1,3,5-triazine, and 1,3,5-tris(3,5-dicyclohexyl-4-hydroxybenzyl) isocyanurate.

In certain embodiments, the at least one antioxidant is selected from aromatic hydroxybenzyl compounds. In certain embodiments, the at least one antioxidant is selected from 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, and 2,4,6-tris(3,5-di-tert-butyl-4-hydroxybenzyl)phenol. In certain embodiments, the at least one antioxidant is selected from benzylphosphonates. In certain embodiments, the at least one antioxidant is selected from dimethyl-2,5-di-tert-butyl-4-hydroxybenzylphosphonate, diethyl-3,5-di-tert-butyl-4-hydroxybenzylphosphonate, dioctadecyl 3,5-di-tert-butyl-4-hydroxybenzylphosphonate, dioctadecyl-5-tert-butyl-4-hydroxy 3-methylbenzylphosphonate, and the calcium salt of the monoethyl ester of 3,5-di-tert-butyl-4-hydroxybenzylphosphonic acid. In certain embodiments, the at least one antioxidant is selected from acylaminophenols. In certain embodiments, the at least one antioxidant is selected from 4-hydroxylauranilide, 4-hydroxystearanilide, and octyl N-(3,5-di-tert-butyl-4-hydroxyphenyl)carbamate.

In certain embodiments, the at least one antioxidant is selected from esters of [3-(3,5-di-tert-butyl-4-hydroxyphenyl)propionic acid with mono- or polyhydric alcohols, such as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, or 4-hydroxymethyl-1-phospha-2,6,7-trioxabicyclo[2.2.2]octane. In certain embodiments, the at least one antioxidant is selected from esters of f3-(5-tert-butyl-4-hydroxy-3-methylphenyl)propionic acid with mono- or polyhydric alcohols, such as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, or 4-hydroxymethyl-1-phospha-2,6,7-trioxabicyclo[2.2.2]octane. In certain embodiments, the at least one antioxidant is selected from esters of 13-(3,5-dicyclohexyl-4-hydroxyphenyl)propionic acid with mono- or polyhydric alcohols, such as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, and 4-hydroxymethyl-1-phospha-2,6,7-trioxabicyclo[2.2.2]octane. In certain embodiments, the at least one antioxidant is selected from esters of 3,5-di-tert-butyl-4-hydroxyphenyl acetic acid with mono- or polyhydric alcohols, such as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, and 4-hydroxymethyl-1-phospha-2,6,7-trioxabicyclo[2.2.2]octane.

Other exemplary, non-limiting examples of suitable antioxidants include those that include nitrogen, such as amides of f3-(3,5-di-tert-butyl-4-hydroxyphenyl)propionic acid, such as N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, and N,N'-bis(3,5-di-tert-butyl-4-hydroxyphenylpropionyl)hydrazine. Even further non-limiting examples of suitable antioxidants include aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,1-trithiamidecane and 2,2,15,15-tetramethyl-5,12-dihydroxy-3,7,10,14-tetrathiahexadecane.

Other exemplary antioxidants include, but are not limited to, those marketed under the commercial tradenames of Vanlube® (R.T. Vanderbilt Corp.), Na-Lube® (King Industries), Irganox® (BASF), Irgalube® (BASF), Ethanox® (Albermarle), and Naugalube® (Chemtura), such as Irganox® L06, Irganox® L55, Irganox® L 57, Irganox® L115, Irganox® L118, Irganox® L134, Irganox® L135, Irganox® L150, Irganox®1010, Irganox®1035, Irgalube® F20, Na-Lube® AO 130, Naugalube®438L, Na-Lube® AO 142, Na-Lube® AO 210, Na-Lube® AO 242, Vanlube® NA, Vanlube® SL, Ethanox®4701, Ethanox®376, Ethanox®4716, Ethanox®4783, Ethanox® 4702, Ethanox®4710, Ethanox®4782J, Ethanox®4727J, Ethanox®4703, and Ethanox®5057.

In certain embodiments, the at least one antioxidant comprises about 0 to about 5 wt. % of the combination or overall composition, such as about 0.01% to about 5%. In certain, the at least one antioxidant comprises about 0 to about 3 wt. % of the combination or overall composition, such as about 0.1 to about 3 wt. %. In certain embodiments, the at least antioxidant is present in amounts of about 0.2, 0.4, 0.6, 0.8, 1.0, 1.2, 1.4, 1.6, 1.8, 2.0, 2.2, 2.4, 2.6, 2.8, or 3.0 wt. % of the combination or overall composition. In certain embodiments, the at least antioxidant is present in amounts of about 1, 2, 3, 4, 5, 6, 7, 8, 9, 10, 11, 12, 13, 14, 15, 16, 17, 18, 19, or 20 wt. % of the combination or overall composition. In certain embodiments, oxidation stability of the oil may be determined by AOM (anaerobic oxidation of methane) or OSI (oxidation stability index) methods known to those skilled in the art.

In certain embodiments, the composition further comprises at least one extreme pressure agent. In certain embodiments, the at least one extreme pressure agent is a phosphorus extreme pressure agent. In certain embodiments, the phosphorus extreme pressure agent comprises one or more compounds selected from phosphoric acid esters, acidic phosphoric acid esters, amine salts of phosphoric acid, amine salts of acidic phosphoric acid esters, amine phosphates, chlorinated phosphoric acid esters, phosphorous acid esters, phosphorylated carboxylic acid compounds, phosphorothionates, and metal salts of phosphorous-containing compounds. In certain embodiments, the at least one extreme pressure agent comprises one or more compounds selected from phosphoric acid esters, acidic phosphoric acid esters, amine salts of acidic phosphoric acid esters, chlorinated phosphoric acid esters, and phosphorous acid esters. In certain embodiments, the at least one extreme pressure agent comprises a phosphorous-containing ester prepared from phosphoric acid and/or phosphorous acid, such as those derived from alkanol or polyether-type alcohols.

Exemplary phosphoric acid esters include, but are not limited to, tripropyl phosphate, tributyl phosphate, tripentyl phosphate, trihexyl phosphate, triheptyl phosphate, trioctyl phosphate, trinonyl phosphate, tridecyl phosphate, triundecyl phosphate, tridodecyl phosphate, tritridecyl phosphate, tritetradecyl phosphate, tripentadecyl phosphate, trihexadecyl phosphate, triheptadecyl phosphate, trioctadecyl phosphate, trioleyl phosphate, triphenyl phosphate, tricresyl phosphate, trixylenyl phosphate, cresyldiphenyl phosphate, and xylyldiphenyl phosphate.

Exemplary acidic phosphoric acid esters include, but are not limited to, phosphoric acid monoalkyl esters such as monopropyl acid phosphate, monobutyl acid phosphate, monopentyl acid phosphate, monohexyl acid phosphate, monoheptyl acid phosphate, monooctyl acid phosphate, monononyl acid phosphate, monodecyl acid phosphate, monoundecyl acid phosphate, monododecyl acid phosphate, monotridecyl acid phosphate, monotetradecyl acid phosphate, monopentadecyl acid phosphate, monohexadecyl acid phosphate, monoheptadecyl acid phosphate, monooctadecyl acid phosphate and monooleyl acid phosphate, and phosphoric acid dialkyl esters and phosphoric acid di(alkyl)aryl esters such as dibutyl acid phosphate, dipentyl acid phosphate, dihexyl acid phosphate, diheptyl acid phosphate, dioctyl acid phosphate, dinonyl acid phosphate, didecyl acid phosphate, diundecyl acid phosphate, didodecyl acid phosphate, ditridecyl acid phosphate, ditetradecyl acid phosphate, dipentadecyl acid phosphate, dihexadecyl acid phosphate, diheptadecyl acid phosphate, dioctadecyl acid phosphate and dioleyl acid phosphate.

Exemplary amine salts of acidic phosphoric acid ester include, but are not limited to, salts of the above-mentioned exemplary acidic phosphoric acid esters with amines such as methylamine, ethylamine, propylamine, butylamine, pentylamine, hexylamine, heptylamine, octylamine, dimethylamine, diethylamine, dipropylamine, dibutylamine, dipentylamine, dihexylamine, diheptylamine, dioctylamine, trimethylamine, triethylamine, tripropylamine, tributylamine, tripentylamine, trihexylamine, triheptylamine, trioctylamine.

Exemplary chlorinated acidic phosphoric acid esters include, but are not limited to, tris dichloro propyl phosphate, tris chloroethyl phosphate, tris chlorophenyl phosphate, and polyoxyalkylene bis[di(chloroalkyl)]phosphate.

Exemplary phosphorous acid esters include, but are not limited to, dibutyl phosphite, dipentyl phosphite, dihexyl phosphite, diheptyl phosphite, dioctyl phosphite, dinonyl phosphite, didecyl phosphite, diundecyl phosphite, didodecyl phosphite, dioleoyl phosphite, diphenyl phosphite, dicresyl phosphite, tributyl phosphite, tripentyl phosphite, trihexyl phosphite, triheptyl phosphite, trioctyl phosphite, trinonyl phosphite, tridecyl phosphite, triundecyl phosphite, tridodecyl phosphite, trioleyl phosphite, triphenyl phosphite, and tricresyl phosphite.

Exemplary phosphorous-containing carboxylic acids include, but are not limited to, compounds represented by Formula A:

Formula A

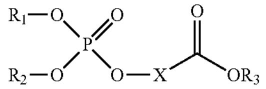

wherein X is an alkylene residue and $R_1$, $R_2$, and $R_3$ are independently selected from hydrogen, optionally substituted alkyl, optionally substituted cycloalkyl, optionally substituted cycloalkylalkyl, optionally substituted aryl, optionally substituted arylalkyl, optionally substituted heteroaryl, optionally substituted heteroarylalkyl, optionally substituted heterocycloalkyl, and optionally substituted heterocycloalkylalkyl.

Exemplary phosphorothionate compounds include, but are not limited to, compounds represented by Formula B:

Formula B

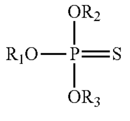

wherein $R_1$, $R_2$, and $R_3$ are independently selected from hydrogen, optionally substituted alkyl, optionally substituted cycloalkyl, optionally substituted cycloalkylalkyl, optionally substituted aryl, optionally substituted arylalkyl, optionally substituted heteroaryl, optionally substituted heteroarylalkyl, optionally substituted heterocycloalkyl, and optionally substituted heterocycloalkylalkyl.

Exemplary amine salts of phosphorous-containing compounds include, but are not limited to, alkylamine or alkanolamine salts of phosphoric acid, butylamine phosphates, propanolamine phosphates, and triethanol, monoethanol, dibutyl, dimethyl, and monoisopropanol amine phosphates.

Exemplary metal salts of phosphorous-containing compounds include, but are not limited to, metal salts of the phorphorous compounds described herein. In certain embodiments, the metal salts of phorphorous compounds are prepared by neutralizing a part or whole of the acidic hydrogen of the phosphorus compound with a metal base. Exemplary metal bases include, but are not limited to, metal oxides, metal hydroxides, metal carbonates, and metal chlorides, wherein said metal is selected from alkali metals such as lithium, sodium, potassium, and cesium, alkali-earth metals such as calcium, magnesium, and barium, and heavy metals such as zinc, copper, iron, lead, nickel, silver, and manganese.

In certain embodiments, the at least one extreme pressure agent is selected from one or more sulfur compounds. In certain embodiments, the at least one extreme pressure agent comprises one or more compounds selected from sulfides and polysulfides, such as benzyldisulfide, bis-(chlorobenzyl)disulfide, dibutyl tetrasulfide, sulfurized oils and fats, sulfurized glyceridic oils, sulfurized fatty acids, sulfurized esters, sulfurized olefins, dihydrocarbyl(poly)sulfides, thiadiazole compounds, alkylthiocarbamoyl compounds, alkylthiocarbamate compounds, thioterpene compounds, dialkyl thiodipropionate compounds, sulfurized mineral oils, zinc dithiocarbamate compounds and molybdenum dithiocarbamates, sulfurized alkylphenols, sulfurized dipentenes, sulfurized terpenes, and sulfurized Diels-Alder adducts. Other exemplary sulfur compounds include, but are not limited to, phosphosulfurized hydrocarbons, such as the reaction product of phosphorus sulfide with turpentine or methyl oleate.

Exemplary dihydrocarbyl(poly)sulfides include, but are not limited to, dibenzyl polysulfides, dinonyl polysulfides, didodecyl polysulfides, dibutyl polysulfides, dioctyl polysulfides, diphenyl polysulfides, and dicyclohexyl polysulfides. Exemplary thiadiazole compounds include, but are not limited to, 1,3,4-thiadiazoles, 1,2,4-thiadiazoles, and 1,4,5-thiadiazoles, such as 2,5-bis(n-hexyldithio)-1,3,4-thiadiazole, 2,5-bis (n-octyldithio)-1,3,4-thiadiazole, 2,5-bis(n-nonyldithio)-1,3,4-thiadiazole, 2,5-bis(1,1,3,3-tetramethylbutyldithio)-1,3,4-thiadiazole, 3,5-bis(n-hexyldithio)-1,2,4-thiadiazole, 3,5-bis(n-octyldithio)-1,2,4-thiadiazole, 3,5-bis (n-nonyldithio)-1,2,4-thiadiazole, 3,5-bis(1,1,3,3-tetramethylbutyldithio)-1,2,4-thiadiazole, 4,5-bis(n-hexyldithio)-1,2,3-thiadiazole, 4,5-bis (n-octyldithio)-1,2,3-thiadiazole, 4,5-bis(n-nonyldithio)-1,2,3-thiadiazole, and 4,5-bis(1,1,3,3-tetramethylbutyldithio)-1,2,3-thiadiazole.

Exemplary alkylthiocarbamoyl compounds include, but are not limited to, bis(dimethylthiocarbamoyl)monosulfide, bis(dibutylthiocarbamoyl)monosulfide, bis(dimethylthiocarbamoyl)disulfide, bis(dibutylthiocarbamoyl)disulfide, bis (diamylthiocarbamoyl)disulfide, and bis(dioctylthiocarbamoyl)disulfide. Exemplary alkylthiocarbamate compounds include, but are not limited to, methylene bis(dibutyldithiocarbamate) and methylene bis[di(2-ethylhexyl)dithiocarbamate]. Exemplary thioterpene compounds include, but are not limited to, reaction products of phosphorus pentasulfide and pinene. Exemplary dialkyl thiodipropionate compounds include, but are not limited to, dilauryl thiodipropionate and distearyl thiodipropionate.

In certain embodiments, the at least one extreme pressure agent is present in amounts of about 0 to about 25 wt. % of the composition. In certain embodiments, the at least one extreme pressure agent is present in amounts of about 0 to about 20, about 0 to about 15, about 0 to about 10, about 0 to about 8, about 0 to about 6, about 0 to about 4, or about 0 to about 2 wt. % of the composition. In certain embodiments, the at least one extreme pressure agent is present in amounts of about 0 to about 5 wt. % of the composition, such as about 0.1 to about 3 wt %. In certain embodiments, the at least one extreme pressure agent is present in amounts of about 1, 2, 3, 4, 5, 6, 7, 8, 9, 10, 11, 12, 13, 14, 15, 16, 17, 18, 19, or 20 wt. % of the composition. In certain embodiments, the at least one extreme pressure agent is present in amounts of about 0.2, 0.4, 0.6, 0.8, 1.0, 1.2, 1.4, 1.6, 1.8, 2.0, 2.2, 2.4, 2.6, 2.8, or 3.0 wt. % of the composition.

In certain embodiments, the composition further comprises at least one antifoaming agent. Exemplary antifoaming agents include, but are not limited to, silicones such as dimethylsilicone and fluorosilicone, and polymers thereof, polyacrylates such as polymethacrylates, and perfluoroalkyl ethers. In certain embodiments, the at least one antifoaming agent is present in amounts of about 0 to about 25 wt. % of the composition. In certain embodiments, the at least one antifoaming agent is present in amounts of about 0 to about 20, about 0 to about 15, about 0 to about 10, about 0 to about 8, about 0 to about 6, about 0 to about 4, or about 0 to about 2 wt. % of the composition. In certain embodiments, the at least one antifoaming agent is present in amounts of about 0 to about 5 wt. % of the composition, such as about 0.1 to about 3 wt %. In certain embodiments, the at least one antifoaming agent is present in amounts of about 1, 2, 3, 4, 5, 6, 7, 8, 9, 10, 11, 12, 13, 14, 15, 16, 17, 18, 19, or 20 wt. % of the composition. In certain embodiments, the at least one antifoaming agent is present in amounts of about 0.2, 0.4, 0.6, 0.8, 1.0, 1.2, 1.4, 1.6, 1.8, 2.0, 2.2, 2.4, 2.6, 2.8, or 3.0 wt. % of the composition.

In certain embodiments, the composition further comprises at least one demulsifier. In certain embodiments, the at least one demulsifier is an anionic surfactant, such as an alkyl-naphthalene sulfonate or an alkyl benzene sulfonate. In certain embodiments, the at least one demulsifier is nonionic. In certain embodiments, the at least one demulsifier is selected from a nonionic alkoxylated alkylphenol resin, a polymer of an alkylene oxide such as polyethylene oxide, polypropylene oxide, a block copolymer of ethylene oxide, or propylene oxide, an ester of an oil soluble acid, and a polyoxyethylene sorbitan. Other exemplary demulsifiers include, but are not limited to, block copolymers of propylene oxide or ethylene oxide and initiators, such as glycerol, phenol, formaldehyde resins, soloxanes, polyamines, and polyols. In certain embodimetns, the polymers contain about 20 to about 50% ethylene oxide. Low molecular weight materials, such as, for example, alkali metal or alkaline earth metal salts of dialkylnaphthalene sulfonic acids, may also useful in certain applications. In certain embodiments, the at least one demulsifier may be present from about 0.01 wt. % to about 10 wt. %, from about 0.05 wt. % to about 5 wt. %, or from about 0.1 wt. % to about 3 wt. % of the composition. In certain embodiments, the at least one demulsifier is present in amounts of about 1, 2, 3, 4, 5, 6, 7, 8, 9, or 10 wt. % of the composition. In certain embodiments, the at least one demulsifier is present in amounts of about 0.2, 0.4, 0.6, 0.8, 1.0, 1.2, 1.4, 1.6, 1.8, 2.0, 2.2, 2.4, 2.6, 2.8, or 3.0 wt. % of the composition.

In certain embodiments, the at least one additive includes at least one antimicrobial agent. In certain embodiments, the at least one antimicrobial agent inhibits the growth of microorganisms. In certain embodiments, the at least one antimicrobial agent is any antimicrobial substance that is compatible with the composition may be blended into the composition. In certain embodiments, compounds that are useful as antioxidants also may be used as antimicrobials. For example, in certain embodiments, phenolic antioxidants such as BHA may also exhibit some activity against one or more of bacteria, molds, viruses and protozoa. In certain embodiments, the at least one antioxidant may be added with at least one antimicrobial agent selected from one or more of potassium sorbate, sorbic acid, and monoglycerides. Other exemplary antimicrobials include, but are not limited to, vitamin E and ascorbyl palmitate, as well as morpholine-based compounds such as 4-(2-nitrobutyl)morpholine, 4,4'-(2-ethyl-2-nitrotrimethylene)dimorpholine and methylene dimorpholine, which may be commercially available under the designations Bioban P-1487™, Bioban CS-1135™, and Kaython™ EDC 1.5 (marketed by Dow Chemical Co.). Other exemplary antimicrobial agents include, but are not limited to, those comprising the material poly(oxy-1,2-ethanediyl(dimethylimino)-1,2-ethanediyl(dimethylimino)-1,2-ethanediyl dichloride, sold under the designation Busan®77 (marketed by Buckman Laboratories, Inc. of Memphis, Tenn.).

In certain embodiments, the at least one additive includes at least one metal chelating agent and/or at least one metal deactivator. Since metals like copper may be present, in certain embodiments the composition may include at least one metal deactivator. Exemplary metal deactivators include, but are not limited to, yellow metal deactivators such as copper and copper alloy deactivators. Exemplary metal deactivators include, but are not limited to, benzotriazoles and derivatives thereof, such as 4- or 5-alkylbenzotriazoles (e.g. triazole), 4,5,6,7-tetrahydrobenzotriazole and 5,5'-methylenebisbenzotriazole, Mannich bases of benzotriazole or triazole, such as 1-[bis(2-ethylhexyl)aminomethyl)triazole and 1-[bis(2-ethylhexyl)aminomethyl)benzotriazole, and alkoxyalkylbenzotriazoles such as 1-(nonyloxymethyl)benzotriazole, 1-(1-butoxyethyl)benzotriazole and 1-(1-cyclohexyloxybutyl)triazole. Additional non-limiting examples include 1,2,4-triazoles and derivatives thereof, such as 3-alkyl(or aryl)-1,2,4-triazoles, and Mannich bases of 1,2,4-triazoles, such as 1-[bis(2-ethylhexyl)aminomethyl-1,2,4-triazole, alkoxyalkyl-1,2,4-triazoles such as 1-(1-butoxyethyl)-1,2,4-triazole, and acylated 3-amino-1,2,4-triazoles, and imidazole derivatives such as 4,4'-methylenebis(2-undecyl-5-methylimidazole) and bis[(N-methyl)imidazol-2-yl]carbinol octyl ether. In certain embodiments, the at least one metal deactivator is selected from 2-mercaptobenzothiazole, 2,5-dimercapto-1,3,4-thiadiazole and derivatives thereof, and 3,5-bis[di(2-ethylhexyl)aminomethyl]-1,3,4-thiadiazolin-2-one. Other exemplary metal deactivators may include amino compounds, such as salicylidenepropylenediamine, salicylaminoguanidine and salts thereof. Exemplary metal deactivators include those available under the trade designation K-Corr® (King Industries), including K-Corr®100 and K-Corr® NF-200.

In certain embodiments, the composition comprises at least one metal deactivator in an amount equal to or lower than about 1 wt. %, such as about 0.1 wt. % to about 0.5 wt. %. In certain embodiments, the composition comprises at least one metal deactivator in an amount of about 0.1, 0.2, 0.3, 0.4, 0.5, 0.6, 0.7, 0.8, 0.9, or 1.0 wt. % of the composition. In certain embodiments, the composition includes a combination of additives, such as a combination of amine and phenolic antioxidants and/or triazole metal deactivators. An exemplary combination includes, but is not limited to, Irganox® L-57 antioxidant, Irganox® L-109 antioxidant, and Irgamet®-30 metal deactivator, which are each commercially available from Ciba-Geigy, Inc. (now BASF).

In certain embodiments, one or more of the optional additives, such as certain metal deactivator packages, may comprise a fatty acid or fatty acid derivative or precursor, which may increase the acid value (e.g., total acid number) of the composition. Without being bound to any particular theory, in certain embodiments, it is believed that increasing the acid value of the composition may result in decreased oxidative stability of the formulation. Accordingly, in certain embodiments, the composition will be substantially free of fatty acid components, such as free fatty acids, and/or have a low acid value.

In certain embodiments is described a method of preparing an estolide composition, said method comprising selecting an estolide base oil; reducing the acid value of the estolide base oil to provide a low-acid estolide base oil; and combining the low-acid estolide base oil with at least one antioxidant. In certain embodiments, reducing the acid value of the estolide base oil to provide a low-acid estolide base oil comprises contacting said estolide base oil with at least one acid-reducing agent. In certain embodiments, the at least one acid-reducing agent is selected from any suitable agent, such as, for example, one or more of activated carbon, magnesium silicate (e.g., Magnesol®), aluminum oxide (e.g., Alumina), silicon dioxide, a zeolite, a basic resin, and an anionic exchange resin. In certain embodiments, the acid value of the at least one estolide base oil is reduced to any of the levels described herein, such as about 0.1 mg KOH/g or lower. In certain embodiments, the combination of the low-acid estolide base oil and the at least one antioxidant will have a time value similar to the times described herein for other estolide base oils when tested in a rotating pressurized vessel oxidation test using ASTM Method 2272-11, such as about 1000 minutes or more.

In certain embodiments, the composition further comprises at least one friction modifier. In certain embodiments, the at least one friction modifier is selected from amine-, imide-, amide-, and fatty acid-type friction modifiers, each of which may comprise at least one alkyl group having 6 to 30 carbon atoms, such as a straight-chain alkyl group having 6 to 30 carbon atoms. Exemplary amine-type friction modifiers include, but are not limited to, straight-chain or branched amines, such as straight-chain aliphatic monoamines, aliphatic alkanolamines, and aliphatic polyamines, and alkyleneoxide adducts of such aliphatic amines. Exemplary imide-type friction modifiers include, but are not limited to, succinimide-type friction modifiers such as mono- and/or bis-succinimides having one or two straight-chain or branched hydrocarbon groups, such as those having hydrocarbon group 6 to 30 or 8 to 18 carbon atoms, and succinimide-modified compounds produced by allowing such succinimides to react with one or more compounds selected from boric acid, phosphoric acid, carboxylic acids such as those having 1 to 20 carbon atoms, and sulfur-containing compounds. Exemplary amide-type friction modifiers include, but are not limited to, fatty acid amide-type friction modifiers such as amides of straight-chain or branched fatty acid (including those having 7 to 31 carbon atoms) and ammonia, aliphatic monoamines, or aliphatic polyamines.

In certain embodiments the at least one friction modifier is a fatty acid-type friction modifier, such as a straight-chain or branched fatty acid, a fatty acid esters of such fatty acids and aliphatic monohydric alcohols or aliphatic polyhydric alcohols, a fatty acid metal salt such as alkaline earth metal salts of such fatty acids (magnesium and calcium salts) and zinc salts of such fatty acids. In certain embodiments, the friction modifier is present from about 0.01 to about 5.0 wt. % of the composition, such as about 0.03 to about 3.0 wt. %. In certain embodiments, the at least one friction modifier is present in amounts of about 0.2, 0.4, 0.6, 0.8, 1.0, 1.2, 1.4, 1.6, 1.8, 2.0, 2.2, 2.4, 2.6, 2.8, or 3.0 wt. % of the composition.

In certain embodiments, the composition further comprises at least one viscosity modifier. In certain embodiments, the at least one viscosity modifier provides high and low temperature operability to the lubricating oil and permits it to remain shear stable at elevated temperatures, while providing acceptable viscosity or fluidity at low temperatures. In certain embodiments, the at least one viscosity modifier comprises one or more compounds selected from high molecular weight hydrocarbon polymers, such as polyesters. In certain embodiments, the at least one viscosity modifier is derivatized to include other properties or functions, such as the addition of dispersancy properties. Exemplary viscosity modifiers include, but are not limited to, polybutene, polyisobutylene (PIB), copolymers of ethylene and propylene, polymethacrylates, methacrylate copolymers, copolymers of an unsaturated dicarboxylic acid and vinyl compound, interpolymers of styrene and acrylic esters, and partially hydrogenated copolymers of styrene/isoprene, styrene/butadiene, and isoprene/butadiene, as well as the partially hydrogenated homopolymers of butadiene and isoprene.

In certain embodiments, the composition comprises at least one polybutene polymer. In certain embodiments, the at least one polybutene polymer comprises a mixture of poly-n-butenes and polyisobutylene, which may result from the polymerization of $C_4$ olefins and generally will have a number average molecular weight of about 300 to 1500, or a polyisobutylene or polybutene having a number average molecular weight of about 400 to 1300. In certain embodiments, the polybutene and/or polyisobutylene may have a number average molecular weight (MW) of about 950. MW may be measured by gel permeation chromatography. Polymers composed of 100% polyisobutylene or 100% poly-n-butene should be understood to fall within the scope of this disclosure and within the meaning of the term "a polybutene polymer". An exemplary polyisobutylene includes "PIB S1054" which has an MW of about 950 and is sold by Infineum USA of Linden, N.J.

In certain embodiments, the at least one polybutene polymer comprises a mixture of polybutenes and polyisobutylene prepared from a $C_4$ olefin refinery stream containing about 6 wt. % to about 50 wt. % isobutylene with the balance a mixture of butene (cis- and trans-) isobutylene and less than 1 wt %. butadiene. For example, the at least one polybutene polymer may be prepared via Lewis acid catalysis from a $C_4$ stream composed of 6-45 wt. % isobutylene, 25-35 wt. % saturated butenes and 15-50 wt. % 1- and 2-butenes. In certain embodiments, the composition comprises from about 0 wt. % to about 80 wt. %, such as about 0 wt. % to about 60 wt. % or about 0 wt. % to about 40 wt. % of the at least one viscosity modifier. In certain embodiments, the at least one viscosity modifier is present in amounts of about 1 wt. % to about 30 wt. %, about 1 wt. % to about 25 wt. %, or about 5 wt. % to about 20 wt. % of the composition. In certain embodiments, the at least one viscosity modifier comprises about 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 30, 35, 40, 45, 50, 55, 60, 65, 70, 75, or 80 wt. % of the composition.

In certain embodiments, the composition further comprises at least one pour point depressant. Exemplary pour point depressants include, but are not limited to, polyvinyl acetate oligomers and polymers and/or acrylic oligomers and polymers, including (meth)acrylates such as those available from Rohmax, Philadelphia, Pa., under the trade designation Viscoplex®. In certain embodiments, the at least one pour point depressant is an alkyl methacrylates with a molecular weight of about 200,000, such as Viscoplex®10-310. Other suitable pour point depressants may include methacrylates available from Functional Products, Macedonia, Ohio, under the trade designation PD-551. In certain embodiments, the at least one pour point depressant is present in the composition from about 0 wt. % to about 5 wt. %, such as about 0.2 wt. % to about 3 wt. %, or about 0.4 wt. % to about 2 wt. %. In certain embodiments, the at least one our point depressant is present in amounts of about 1, 2, 3, 4, or 5 wt. % of the composition. In certain embodiments, the at least one pour point depressant is present in amounts of about 0.2, 0.4, 0.6, 0.8, 1.0, 1.2, 1.4, 1.6, 1.8, 2.0, 2.2, 2.4, 2.6, 2.8, or 3.0 wt. % of the composition.

In certain embodiments, the composition comprises at least one colorant. In certain embodiments, the at least one colorant is selected from dyes and pigments. In certain embodiments, any known dyes and/or pigments can be used, such as those available commercially as food additives. In certain embodiments, the dyes and pigments may be selected from oil soluble dyes and pigments. In certain embodiments, the at least one colorant is present in the composition in minor amounts, such as less than about 1 ppm.

In certain embodiments, composition comprises an estolide base oil. In certain embodiments, the composition comprises a combination of an estolide base oil and at least one antioxidant. In certain embodiments, the composition and/or combination has a time of at least 200 minutes when tested in a rotating pressurized vessel oxidation test using ASTM Method 2272-11. In certain embodiments, the composition and/or combination has a time of at least 300 minutes when tested in a rotating pressurized vessel oxidation test using ASTM Method 2272-11. In certain embodiments, the composition and/or combination has a time of at least 400 minutes when tested in a rotating pressurized vessel oxidation test using ASTM Method 2272-11. In certain embodiments, the composition and/or combination has a time of at least 420, 440, 460, or even 480 minutes when tested in a rotating pressurized vessel oxidation test using ASTM Method 2272-11. In certain embodiments, the composition and/or combination has a time of at least 500, 520, 540, 560, 580, 600, 620, 640, 660, 680, 700, 720, 740, 760, 780, 800, 820, 840, 860, 880, 900, 920, 940, 960, or even 980 minutes when tested in a rotating pressurized vessel oxidation test using ASTM Method 2272-11. In certain embodiments, the composition and/or combination has a time of at least 1000, 1100, 1200, 1300, 1400, or even 1500 minutes when tested in a rotating pressurized vessel oxidation test using ASTM Method 2272-11.

In certain embodiments, the composition and/or combination has an oxidation onset temperature of at least 200° C. as determined by non-isothermal pressurized-differential scanning calorimetry under dynamic $O_2$ conditions. In certain embodiments, the composition and/or combination has an oxidation onset temperature of at least 205° C., 210° C., 215° C., 220° C., 225° C., 230° C., 235° C., 240° C., 245° C., 250° C., 255° C., 260° C., 265° C., 270° C., 275° C., 280° C., 285° C., 290° C., 295° C., 300° C., 305° C., 310° C., 315° C., 320° C., or even 325° C. as determined by non-isothermal pressurized-differential scanning calorimetry under dynamic $O_2$ conditions.

In certain embodiments, the composition comprises a co-blend of at least one estolide base oil and at least one other base oil selected from polyalphaolefins (PAOs), synthetic esters such as polyol esters, polyalkylene glycols (PAGs), oil soluble polyalkylene glycols (OSPs), mineral oils (Groups I, II, and III), vegetable and animal-based oils (e.g., mono, di-, and tri-glycerides), and fatty-acid esters. In certain embodiments, the composition comprises at least one estolide base oil and at least one OSP. In certain embodiments, the at least one OSP is prepared from reacting an alcohol with a mixed butylene oxide and propylene oxide feed. In certain embodiments, the alcohol is selected from one or more $C_8$-$C_{20}$ alcohols. In certain embodiments, the ratio of butylene oxide to propylene oxide is from about 3:1 to about 1:3. In certain embodiments, the at least one OSP may provide increased hydrolytic stability to the estolide-containing composition. Exemplary OSPs include, but are not limited to, those marketed under the trade designation UCON by Dow.

The present disclosure further relates to methods of making estolides according to Formula I, II, and III. By way of example, the reaction of an unsaturated fatty acid with an organic acid and the esterification of the resulting free acid estolide are illustrated and discussed in the following Schemes 1 and 2. The particular structural formulas used to illustrate the reactions correspond to those for synthesis of compounds according to Formula I and III; however, the methods apply equally to the synthesis of compounds according to Formula II, with use of compounds having structure corresponding to $R_3$ and $R_4$ with a reactive site of unsaturation.

As illustrated below, compound 100 represents an unsaturated fatty acid that may serve as the basis for preparing the estolide compounds described herein.

Scheme 1

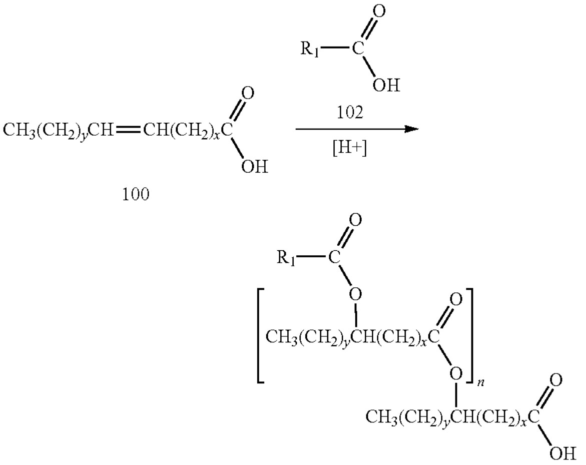

100

102

104

In Scheme 1, wherein x is, independently for each occurrence, an integer selected from 0 to 20, y is, independently for each occurrence, an integer selected from 0 to 20, n is an integer greater than or equal to 1, and $R_1$ is an optionally substituted alkyl that is saturated or unsaturated, and branched or unbranched, unsaturated fatty acid 100 may be combined with compound 102 and a proton from a proton source to form free acid estolide 104. In certain embodiments, compound 102 is not included, and unsaturated fatty acid 100 may be exposed alone to acidic conditions to form free acid estolide 104, wherein $R_1$ would represent an unsaturated alkyl group. In certain embodiments, if compound 102 is included in the reaction, $R_1$ may represent one or more optionally substituted alkyl residues that are saturated or unsaturated and branched or unbranched. Any suitable proton source may be implemented to catalyze the formation of free acid estolide 104, including but not limited to homogenous acids and/or strong acids like hydrochloric acid, sulfuric acid, perchloric acid, nitric acid, triflic acid, and the like.

Scheme 2

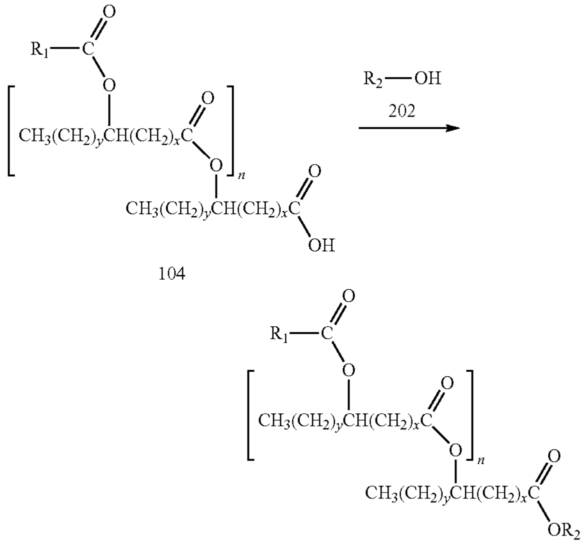

104

204

Similarly, in Scheme 2, wherein x is, independently for each occurrence, an integer selected from 0 to 20, y is, independently for each occurrence, an integer selected from 0 to 20, n is an integer greater than or equal to 1, and $R_1$ and $R_2$ are each an optionally substituted alkyl that is saturated or unsaturated, and branched or unbranched, free acid estolide 104 may be esterified by any suitable procedure known to those of skilled in the art, such as acid-catalyzed reduction with alcohol 202, to yield esterified estolide 204. Other exemplary methods may include other types of Fischer esterification, such as those using Lewis acid catalysts such as $BF_3$.

In all of the foregoing examples, the compounds described may be useful alone, as mixtures, or in combination with other compounds, compositions, and/or materials.

Methods for obtaining the novel compounds described herein will be apparent to those of ordinary skill in the art, suitable procedures being described, for example, in the examples below, and in the references cited herein.

EXAMPLES

Analytics

Nuclear Magnetic Resonance: NMR spectra were collected using a Bruker Avance 500 spectrometer with an absolute frequency of 500.113 MHz at 300 K using $CDCl_3$ as the solvent. Chemical shifts were reported as parts per million from tetramethylsilane. The formation of a secondary ester link between fatty acids, indicating the formation of estolide, was verified with $^1$H NMR by a peak at about 4.84 ppm.

Estolide Number (EN): The EN was measured by GC analysis. It should be understood that the EN of a composition specifically refers to EN characteristics of any estolide compounds present in the composition. Accordingly, an estolide composition having a particular EN may also comprise other components, such as natural or synthetic additives, other non-estolide base oils, fatty acid esters, e.g., triglycerides, and/or fatty acids, but the EN as used herein, unless otherwise indicated, refers to the value for the estolide fraction of the estolide composition.

Iodine Value (IV): The iodine value is a measure of the degree of total unsaturation of an oil. IV is expressed in terms of centigrams of iodine absorbed per gram of oil sample. Therefore, the higher the iodine value of an oil the higher the level of unsaturation is of that oil. The IV may be measured and/or estimated by GC analysis. Where a composition includes unsaturated compounds other than estolides as set forth in Formula I, II, and III, the estolides can be separated from other unsaturated compounds present in the composition prior to measuring the iodine value of the constituent estolides. For example, if a composition includes unsaturated fatty acids or triglycerides comprising unsaturated fatty acids, these can be separated from the estolides present in the composition prior to measuring the iodine value for the one or more estolides.

Acid Value: The acid value is a measure of the total acid present in an oil. Acid value may be determined by any suitable titration method known to those of ordinary skill in the art. For example, acid values may be determined by the amount of KOH that is required to neutralize a given sample of oil, and thus may be expressed in terms of mg KOH/g of oil.

Gas Chromatography (GC): GC analysis was performed to evaluate the estolide number (EN) and iodine value (IV) of the estolides. This analysis was performed using an Agilent 6890N series gas chromatograph equipped with a flame-ionization detector and an autosampler/injector along with an SP-2380 30 m×0.25 mm i.d. column.

The parameters of the analysis were as follows: column flow at 1.0 mL/min with a helium head pressure of 14.99 psi; split ratio of 50:1; programmed ramp of 120-135° C. at 20° C./min, 135-265° C. at 7° C./min, hold for 5 min at 265° C.; injector and detector temperatures set at 250° C.

Measuring EN and IV by GC: To perform these analyses, the fatty acid components of an estolide sample were reacted with MeOH to form fatty acid methyl esters by a method that left behind a hydroxy group at sites where estolide links were once present. Standards of fatty acid methyl esters were first analyzed to establish elution times.

Sample Preparation: To prepare the samples, 10 mg of estolide was combined with 0.5 mL of 0.5M KOH/MeOH in a vial and heated at 100° C. for 1 hour. This was followed by the addition of 1.5 mL of 1.0 M $H_2SO_4$/MeOH and heated at 100° C. for 15 minutes and then allowed to cool to room temperature. One (1) mL of $H_2O$ and 1 mL of hexane were then added to the vial and the resulting liquid phases were mixed thoroughly. The layers were then allowed to phase separate for 1 minute. The bottom $H_2O$ layer was removed and discarded. A small amount of drying agent ($Na_2SO_4$ anhydrous) was then added to the organic layer after which the organic layer was then transferred to a 2 mL crimp cap vial and analyzed.

EN Calculation: The EN is measured as the percent hydroxy fatty acids divided by the percent non-hydroxy fatty acids. As an example, a dimer estolide would result in half of the fatty acids containing a hydroxy functional group, with the other half lacking a hydroxyl functional group. Therefore, the EN would be 50% hydroxy fatty acids divided by 50% non-hydroxy fatty acids, resulting in an EN value of 1 that corresponds to the single estolide link between the capping fatty acid and base fatty acid of the dimer.

IV Calculation: The iodine value is estimated by the following equation based on ASTM Method D97 (ASTM International, Conshohocken, Pa.):

$$IV = \sum 100 \times \frac{A_f \times MW_I \times db}{MW_f}$$

$A_f$=fraction of fatty compound in the sample $MW_I$=253.81, atomic weight of two iodine atoms added to a double bond db=number of double bonds on the fatty compound $MW_f$=molecular weight of the fatty compound The properties of exemplary estolide compounds and compositions described herein are identified in the following examples and tables.

Other Measurements: Except as otherwise described, pour point is measured by ASTM Method D97-96a, cloud point is measured by ASTM Method D2500, viscosity/kinematic viscosity is measured by ASTM Method D445-97, viscosity index is measured by ASTM Method D2270-93 (Reapproved 1998), specific gravity is measured by ASTM Method D4052, fire point and flash point are measured by ASTM Method D92, evaporative loss is measured by ASTM Method D5800, vapor pressure is measured by ASTM Method D5191, rotating pressure vessel oxidation testing is measured by ASTM Method 2272-11, and acute aqueous toxicity is measured by Organization of Economic Cooperation and Development (OECD) 203.

Example 1

The acid catalyst reaction was conducted in a 50 gallon Pfaudler RT-Series glass-lined reactor. Oleic acid (65 Kg, OL 700, Twin Rivers) was added to the reactor with 70% perchloric acid (992.3 mL, Aldrich Cat#244252) and heated to 60° C. in vacuo (10 torr abs (Torr absolute; 1 torr=~1 mmHg)) for 24 hrs while continuously being agitated. After 24 hours the vacuum was released. 2-Ethylhexanol (29.97 Kg) was then added to the reactor and the vacuum was restored. The reaction was allowed to continue under the same conditions (60° C., 10 torr abs) for 4 more hours. At which time, KOH (645.58 g) was dissolved in 90% ethanol/water (5000 mL, 90% EtOH by volume) and added to the reactor to quench the acid. The solution was then allowed to cool for approximately 30 minutes. The contents of the reactor were then pumped through a 1 micron (μ) filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1μ filter back into the reactor. The reactor was heated to 60° C. in vacuo (10 torr abs) until all ethanol and water ceased to distill from solution. The reactor was then heated to 100° C. in vacuo (10 torr abs) and that temperature was maintained until the 2-ethylhexanol ceased to distill from solution. The remaining material was then distilled using a Myers 15 Centrifugal Distillation still at 200° C. under an absolute pressure of approximately 12 microns (0.012 torr) to remove all monoester material leaving behind estolides (Ex. 1). Certain data are reported below in Tables 1 and 8.

Example 2

The acid catalyst reaction was conducted in a 50 gallon Pfaudler RT-Series glass-lined reactor. Oleic acid (50 Kg, OL 700, Twin Rivers) and whole cut coconut fatty acid (18.754 Kg, TRC 110, Twin Rivers) were added to the reactor with 70% perchloric acid (1145 mL, Aldrich Cat#244252) and heated to 60° C. in vacuo (10 torr abs) for 24 hrs while continuously being agitated. After 24 hours the vacuum was released. 2-Ethylhexanol (34.58 Kg) was then added to the reactor and the vacuum was restored. The reaction was allowed to continue under the same conditions (60° C., 10 torr abs) for 4 more hours. At which time, KOH (744.9 g) was dissolved in 90% ethanol/water (5000 mL, 90% EtOH by volume) and added to the reactor to quench the acid. The solution was then allowed to cool for approximately 30 minutes. The contents of the reactor were then pumped through a 1μ filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1μ filter back into the reactor. The reactor was heated to 60° C. in vacuo (10 torr abs) until all ethanol and water ceased to distill from solution. The reactor was then heated to 100° C. in vacuo (10 torr abs) and that temperature was maintained until the 2-ethylhexanol ceased to distill from solution. The remaining material was then distilled using a Myers 15 Centrifugal Distillation still at 200° C. under an absolute pressure of approximately 12 microns (0.012 torr) to remove all monoester material leaving behind estolides (Ex. 2). Certain data are reported below in Tables 2 and 7.

Example 3

The estolides produced in Example 1 (Ex. 1) were subjected to distillation conditions in a Myers 15 Centrifugal Distillation still at 300° C. under an absolute pressure of approximately 12 microns (0.012 torr). This resulted in a primary distillate having a lower EN average (Ex. 3A), and a distillation residue having a higher EN average (Ex. 3B). Certain data are reported below in Tables 1 and 8.

TABLE 1

| Estolide Base Stock | EN | Pour Point (° C.) | Iodine Value (cg/g) |
|---|---|---|---|
| Ex. 3A | 1.35 | −32 | 31.5 |
| Ex. 1 | 2.34 | −40 | 22.4 |
| Ex. 3B | 4.43 | −40 | 13.8 |

Example 4

Estolides produced in Example 2 (Ex. 2) were subjected to distillation conditions in a Myers 15 Centrifugal Distillation still at 300° C. under an absolute pressure of approximately 12 microns (0.012 torr). This resulted in a primary distillate having a lower EN average (Ex. 4A), and a distillation residue having a higher EN average (Ex. 4B). Certain data are reported below in Tables 2 and 7.

TABLE 2

| Estolide Base Stock | EN | Pour Point (° C.) | Iodine Value (cg/g) |
|---|---|---|---|
| Ex. 4A | 1.31 | −30 | 13.8 |
| Ex. 2 | 1.82 | −33 | 13.2 |
| Ex. 4B | 3.22 | −36 | 9.0 |

Example 5

Estolides produced by the method set forth in Example 1 were subjected to distillation conditions (ASTM D-6352) at 1 atm (atmosphere) over the temperature range of about 0° C. to about 710° C., resulting in 10 different estolide cuts recovered at increasing temperatures The amount of material distilled from the sample in each cut and the temperature at which each cut distilled (and recovered) are reported below in Table 3:

TABLE 3

| Cut (% of total) | Temp. (° C.) |
|---|---|
| 1 (1%) | 416.4 |
| 2 (1%) | 418.1 |
| 3 (3%) | 420.7 |
| 4 (20%) | 536.4 |
| 5 (25%) | 553.6 |
| 6 (25%) | 618.6 |
| 7 (20%) | 665.7 |
| 8 (3%) | 687.6 |
| 9 (1%) | 700.6 |
| 10 (1%) | 709.1 |

Example 6

Estolides made according to the method of Example 2 were subjected to distillation conditions (ASTM D-6352) at 1 atm over the temperature range of about 0° C. to about 730° C., which resulted in 10 different estolide cuts. The amount of each cut and the temperature at which each cut was recovered are reported in Table 4.

TABLE 4

| Cut (% of total) | Temp. (° C.) |
|---|---|
| 1 (1%) | 417.7 |
| 2 (1%) | 420.2 |
| 3 (3%) | 472.0 |
| 4 (5%) | 509.7 |
| 5 (15%) | 533.7 |
| 6 (25%) | 583.4 |
| 7 (25%) | 636.4 |
| 8 (5%) | 655.4 |
| 9 (5%) | 727.0 |
| 10 (15%) | >727.0 |

Example 7

Estolide base oil 4B (from Example 4) was subjected to distillation conditions (ASTM D-6352) at 1 atm over the temperature range of about 0° C. to about 730° C., which resulted in 9 different estolide cuts. The amount of each cut and the temperature at which each cut was recovered are reported in Table 5a.

TABLE 5a

| Cut (% of total) | Temp. (° C.) |
|---|---|
| 1 (1%) | 432.3 |
| 2 (1%) | 444.0 |
| 3 (3%) | 469.6 |
| 4 (5%) | 521.4 |
| 5 (15%) | 585.4 |
| 6 (25%) | 617.1 |
| 7 (25%) | 675.1 |

TABLE 5a-continued

| Cut (% of total) | Temp. (° C.) |
|---|---|
| 8 (5%) | 729.9 |
| 9 (20%) | >729.9 |

Example 8

Estolides were made according to the method set forth in Example 1, except that the 2-ethylhexanol esterifying alcohol used in Example 1 was replaced with various other alcohols. Alcohols used for esterifiction include those identified in Table 5b below. The properties of the resulting estolides are set forth in Table 9.

TABLE 5b

| Alcohol | Structure |
|---|---|
| Jarcol ™ I-18CG | iso-octadecanol |
| Jarcol ™ I-12 | 2-butyloctanol |
| Jarcol ™ I-20 | 2-octyldodecanol |
| Jarcol ™ I-16 | 2-hexyldecanol |
| Jarcol ™ 85BJ | cis-9-octadecen-1-ol |
| Fineoxocol ®180 | 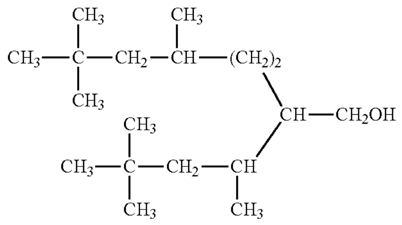 |
| Jarcol ™ I-18T | 2-octyldecanol |

Example 9

Estolides were made according to the method set forth in Example 2, except the 2-ethylhexanol esterifying alcohol was replaced with isobutanol. The properties of the resulting estolides are set forth in Table 9.

Example 10

Estolides of Formula I, II, and III are prepared according to the method set forth in Examples 1 and 2, except that the 2-ethylhexanol esterifying alcohol is replaced with various other alcohols. Alcohols to be used for esterification include those identified in Table 6 below. Esterifying alcohols to be used, including those listed below, may be saturated or unsaturated, and branched or unbranched, or substituted with one or more alkyl groups selected from methyl, ethyl, propyl, isopropyl, butyl, isobutyl, sec-butyl, tert-butyl, pentyl, isopentyl, neopentyl, hexyl, isohexyl, and the like, to form a branched or unbranched residue at the $R_2$ position. Examples of combinations of esterifying alcohols and $R_2$ Substituents are set forth below in Table 6:

TABLE 6

| Alcohol | $R_2$ Substituents |
|---|---|
| $C_1$ alkanol | methyl |
| $C_2$ alkanol | ethyl |
| $C_3$ alkanol | n-propyl, isopropyl |

TABLE 6-continued

| Alcohol | $R_2$ Substituents |
|---|---|
| $C_4$ alkanol | n-butyl, isobutyl, sec-butyl |
| $C_5$ alkanol | n-pentyl, isopentyl neopentyl |
| $C_6$ alkanol | n-hexyl, 2-methyl pentyl, 3-methyl pentyl, 2,2-dimethyl butyl, 2,3-dimethyl butyl |
| $C_7$ alkanol | n-heptyl and other structural isomers |
| $C_8$ alkanol | n-octyl and other structural isomers |
| $C_9$ alkanol | n-nonyl and other structural isomers |
| $C_{10}$ alkanol | n-decanyl and other structural isomers |
| $C_{11}$ alkanol | n-undecanyl and other structural isomers |
| $C_{12}$ alkanol | n-dodecanyl and other structural isomers |
| $C_{13}$ alkanol | n-tridecanyl and other structural isomers |
| $C_{14}$ alkanol | n-tetradecanyl and other structural isomers |
| $C_{15}$ alkanol | n-pentadecanyl and other structural isomers |
| $C_{16}$ alkanol | n-hexadecanyl and other structural isomers |
| $C_{17}$ alkanol | n-heptadecanyl and other structural isomers |
| $C_{18}$ alkanol | n-octadecanyl and other structural isomers |
| $C_{19}$ alkanol | n-nonadecanyl and other structural isomers |
| $C_{20}$ alkanol | n-icosanyl and other structural isomers |
| $C_{21}$ alkanol | n-heneicosanyl and other structural isomers |
| $C_{22}$ alkanol | n-docosanyl and other structural isomers |

TABLE 7

| PROPERTY | ADDITIVES | ASTM METHOD | Ex. 4A | Ex. 2 | Ex. 4B |
|---|---|---|---|---|---|
| Color | None | — | Light Gold | Amber | Amber |
| Specific Gravity (15.5° C.), g/ml | None | D 4052 | 0.897 | 0.904. | 0.912 |
| Viscosity-Kinematic at 40° C., cSt | None | D 445 | 32.5 | 65.4 | 137.3 |

TABLE 7-continued

| PROPERTY | ADDITIVES | ASTM METHOD | Ex. 4A | Ex. 2 | Ex. 4B |
|---|---|---|---|---|---|
| Viscosity-Kinematic at 100° C., cSt | None | D 445 | 6.8 | 11.3 | 19.9 |
| Viscosity Index | None | D 2270 | 175 | 167 | 167 |
| Pour Point, ° C. | None | D 97 | −30 | −33 | −36 |
| Cloud Point, ° C. | None | D 2500 | −30 | −32 | −36 |
| Flash Point, ° C. | None | D 92 | 278 | 264 | 284 |
| Fire Point, ° C. | None | D 92 | 300 | 300 | 320 |
| Evaporative Loss (NOACK), wt. % | None | D 5800 | 1.9 | 1.4 | 0.32 |
| Vapor Pressure - Reid (RVP), psi | None | D 5191 | ≈0 | ≈0 | ≈0 |

TABLE 8

| PROPERTY | ADDITIVES | ASTM METHOD | Ex. 3A | Ex. 1 | Ex. 3B |
|---|---|---|---|---|---|
| Color | None | — | Light Gold | Amber | Amber |
| Specific Gravity (15.5° C.), g/ml | None | D 4052 | 0.897 | 0.906 | 0.917 |
| Viscosity - Kinematic at 40° C., cSt | None | D 445 | 40.9 | 91.2 | 211.6 |
| Viscosity - Kinematic at 100° C., cSt | None | D 445 | 8.0 | 14.8 | 27.8 |
| Viscosity Index | None | D 2270 | 172 | 170 | 169 |
| Pour Point, ° C. | None | D 97 | −32 | −40 | −40 |
| Cloud Point, ° C. | None | D 2500 | −32 | −33 | −40 |
| Flash Point, ° C. | None | D 92 | 278 | 286 | 306 |
| Fire Point, ° C. | None | D 92 | 300 | 302 | 316 |
| Evaporative Loss (NOACK), wt. % | None | D 5800 | 1.4 | 0.8 | 0.3 |
| Vapor Pressure - Reid (RVP), psi | None | D 5191 | ≈0 | ≈0 | ≈0 |

TABLE 9

| Example # | Alcohol | Estimated EN (approx.) | Pour Pt. ° C. | Cloud Pt. ° C. | Visc. @ 40° C. | Visc. @ 100° C. | Visc. Index |
|---|---|---|---|---|---|---|---|
| 8 | Jarcol ™ I-18CG | 2.0-2.6 | −15 | −13 | 103.4 | 16.6 | 174 |
| 8 | Jarcol ™ I-12 | 2.0-2.6 | −39 | −40 | 110.9 | 16.9 | 166 |
| 8 | Jarcol ™ I-20 | 2.0-2.6 | −42 | <−42 | 125.2 | 18.5 | 166 |
| 8 | Jarcol ™ I-16 | 2.0-2.6 | −51 | <−51 | 79.7 | 13.2 | 168 |
| 8 | Jarcol ™ 85BJ | 2.0-2.6 | −15 | −6 | 123.8 | 19.5 | 179 |
| 8 | Fineoxocol ® 180 | 2.0-2.6 | −39 | −41 | 174.2 | 21.1 | 143 |
| 8 | Jarcol ™ I-18T | 2.0-2.6 | −42 | <−42 | 130.8 | 19.2 | 167 |
| 8 | Isobutanol | 2.0-2.6 | −36 | −36 | 74.1 | 12.6 | 170 |
| 9 | Isobutanol | 1.5-2.2 | −36 | −36 | 59.5 | 10.6 | 170 |

Example 11

Saturated and unsaturated estolides having varying acid values were subjected to several corrosion and deposit tests. These tests included the High Temperature Corrosion Bench Test (HTCBT) for several metals, the ASTM D130 corrosion test, and the MHT-4 TEOST (ASTM D7097) test for correlating piston deposits. The estolides tested having higher acid values (0.67 mg KOH/g) were produced using the method set forth in Examples 1 and 4 for producing Ex. 1 and Ex. 4A (Ex. 1* and Ex. 4A* below). The estolides tested having lower acid values (0.08 mg KOH/g) were produced using the method set forth in Examples 1 and 4 for producing Ex. 1 and Ex. 4A except the crude free-acid estolide was worked up and purified prior to esterification with $BF_3$.$OET_2$ (0.15 equiv.; reacted with estolide and 2-EH in Dean Stark trap at 80° C. in vacuo (10 torr abs) for 12 hrs while continuously being agitated; crude reaction product washed 4× $H_20$; excess 2-EH removed by heating washed reaction product to 140° C. in vacuo (10 torr abs) for 1 hr) (Ex. 4A# below). Estolides having an IV of 0 were hydrogenated via 10 wt. % palladium embedded on carbon at 75° C. for 3 hours under a pressurized hydrogen atmosphere (200 psig) (Ex. 4A*H and Ex. 4A#H below) The corrosion and deposit tests were performed with a Dexos™ additive package. Results were compared against a mineral oil standard:

TABLE 10

| | Standard | Ex. 1* Estolide | Ex. 4A* Estolide | Ex. 4A*H Estolide | Ex. 4A# Estolide | Ex. 4A#H Estolide |
|---|---|---|---|---|---|---|
| Acid Value (mg KOH/g) | — | ~0.7 | 0.67 | 0.67 | 0.08 | 0.08 |
| Iodine Value (IV) | — | ~45 | 16 | 0 | 16 | 0 |
| HTCBT Cu | 13 | 739 | 279 | 60 | 9.3 | 13.6 |
| HTCBT Pd | 177 | 11,639 | 1,115 | 804 | 493 | 243 |
| HTCBT Sn | 0 | 0 | 0 | 0 | 0 | 0 |
| ASTM D130 | 1A | 4B | 3A | 1B | 1A | 1A |
| MHT-4 | 18 | 61 | 70 | 48 | 12 | 9.3 |

Example 12

"Ready" and "ultimate" biodegradability of the estolide produced in Ex. 1 was tested according to standard OECD procedures. Results of the OECD biodegradability studies are set forth below in Table 11:

TABLE 11

| | 301D 28-Day (% degraded) | 302D Assay (% degraded) |
|---|---|---|
| Canola Oil | 86.9 | 78.9 |
| Ex. 1 Base Stock | 64.0 | 70.9 |

Example 13

The Ex. 1 estolide base stock from Example 1 was tested under OECD 203 for Acute Aquatic Toxicity. The tests showed that the estolides are nontoxic, as no deaths were reported for concentration ranges of 5,000 mg/L and 50,000 mg/L.

Example 14

Estolides were prepared according to the method set forth in Example 2, except the reaction was initially charged with 41.25 Kg of Oleic acid and 27.50 Kg of whole cut coconut fatty acids. Properties of the resulting estolides are set forth below in Table 12.

Example 15

The estolides produced in Example 14 (Ex. 14) were subjected to distillation conditions in a Myers 15 Centrifugal Distillation still at 300° C. under an absolute pressure of approximately 12 microns (0.012 torr). This resulted in a primary distillate having a lower viscosity (Ex. 15A), and a distillation residue having a higher viscosity (Ex. 15B). Properties of the resulting estolides are set forth below in Table 12.

TABLE 12

| Estolide Base Stock | EN | Acid Value (mg KOH/g) |
|---|---|---|
| Ex. 15A | 1.31 | >0.5 |
| Ex. 14 | 1.86 | >0.5 |
| Ex. 15B | 2.94 | >0.5 |

Example 16

Estolides were prepared according to the methods set forth in Examples 14 and 15 to provide estolide products of Ex. 14, Ex. 15A, and Ex. 15B, which were subsequently subjected to a basic anionic exchange resin wash to lower the estolides' acid value: separately, each of the estolide products (1 equiv) were added to a 30 gallon stainless steel reactor (equipped with an impeller) along with 10 wt. % of Amberlite™ IRA-402 resin. The mixture was agitated for 4-6 hrs, with the tip speed of the impeller operating at no faster than about 1200 ft/min. After agitation, the estolide/resin mixture was filtered, and the recovered resin was set aside. Properties of the resulting low-acid estolides are set forth below in Table 13, which are labeled Ex. 14*, Ex. 15A*, and Ex. 15B*.

Example 17

Estolides were prepared according to the methods set forth in Examples 15. The resulting Ex. 15A estolides were subsequently hydrogenated via 10 wt. % palladium embedded on carbon at 75° C. for 3 hours under a pressurized hydrogen atmosphere to provide hydrogenated estolide compounds (Ex. 17). The hydrogenated Ex. 17 estolides were then subjected to a basic anionic exchange resin wash according to the method set forth in Example 16 to provide low-acid estolides (Ex. 17*). The properties of the resulting low-acid Ex. 17* estolides are set forth below in Table 13.

TABLE 13

| Property | Additives | ASTM METHOD | Ex. 15A* | Ex. 17* | Ex. 14* | Ex. 15B* |
|---|---|---|---|---|---|---|
| Color | None | — | Light Gold | Light Gold | Amber | Amber |
| Specific Gravity (15.5° C.), g/ml | None | D 4052 | 0.897 | 0.897 | — | 0.912 |
| Viscosity-Kinematic at 40° C., cSt | None | D 445 | 35.3 | 35.3 | 52.3 | 137.3 |
| Viscosity-Kinematic at 100° C., cSt | None | D 445 | 7.2 | 7.2 | 9.6 | 19.9 |
| Viscosity Index | None | D 2270 | 172 | 172 | 170 | 167 |
| Iodine Value | None | (GC, estimated) | 13 | 0 | 12 | 7 |
| Pour Point, ° C. | None | D 97 | −30 | −21 | −36 | −36 |
| Cloud Point, ° C. | None | D 2500 | −27 | −16 | −29 | −33 |
| Flash Point, ° C. | None | D 92 | 280 | 280 | 280 | 284 |
| Fire Point, ° C. | None | D 92 | 300 | 300 | 300 | 320 |
| Evaporative Loss (NOACK), wt. % | None | D 5800 | 1.9 | 1.9 | — | 1.1 |
| Copper Corrosion | None | D 130 | 1A | 1A | 1A | 1A |
| Acid Value, mg KOH/g | None | D 664 | <0.10 | <0.10 | <0.10 | <0.10 |

Example 18

Estolides were prepared according to the methods set forth above. To the resulting estolides were added various antioxidants and antioxidant-containing additive packages. Heat and stifling were applied where necessary to effect dissolution of the antioxidant and/or additive package in the estolide base oil. The oxidative stability of the resulting formulated estolides was then tested via rotating pressure vessel oxidative stability test (RPVOT)—ASTM 2272-11 at 150° C. Results for the various formulations are set forth below in Table 14, along with comparative testing results for several non-estolide base oil formulations.

TABLE 14

| Form. No. | Base Oil (wt. %) | Phenolic Antioxidant [tradename] (wt. %) | Amine Antioxidant [tradename] (wt. %) | RPVOT ASTM 2272-11 (mins) |
|---|---|---|---|---|
| 1 | Ex. 17* estolide (100) | — | — | 28 |
| 2 | Ex. 17* estolide (99.5) | 2,6-di-t-butylphenol [Na-Lube ® AO-210] (0.5) | — | 432 |
| 3 | Ex. 17* estolide (99) | 2,6-di-t-butylphenol [Na-Lube ® AO-210] (1) | — | 521 |
| 4 | Ex. 17* estolide (99.5) | — | Nonylated diphenylamine [Na-Lube ® AO-130] (0.5) | 1245 |
| 5 | Ex. 17* estolide (99) | — | Nonylated diphenylamine [Na-Lube ® AO-130] (1) | 1194 |
| 6 | Ex. 17* estolide (99.5) | 2,6-di-t-butylphenol [Na-Lube ® AO-210] (0.25) | Nonylated diphenylamine [Na-Lube ® AO-130] (0.25) | 1268 |
| 7 | Ex. 17* estolide (99.25) | 2,6-di-t-butylphenol [Na-Lube ® AO-210] (0.375) | Nonylated diphenylamine [Na-Lube ® AO-130] (0.375) | 1423 |
| 8 | Ex. 17* estolide (99) | 2,6-di-t-butylphenol [Na-Lube ® AO-210] (0.5) | Nonylated diphenylamine [Na-Lube ® AO-130] (0.5) | 1464 |
| 9 | Ex. 17* estolide (98.75) | 2,6-di-t-butylphenol [Na-Lube ® AO-210] (0.625) | Nonylated diphenylamine [Na-Lube ® AO-130] (0.625) | 1460 |
| 10 | Ex. 17* estolide (98) | 2,6-di-t-butylphenol [Na-Lube ® AO-210] (1) | Nonylated diphenylamine [Na-Lube ® AO-130] (1) | 1231 |
| 11 | Ex. 17* estolide (99) | Alkyl 3-(3',5'-di-t-butyl-4'-hydroxyphenyl) propionate [Na-Lube ® AO-242] (0.5) | Nonylated diphenylamine [Na-Lube ® AO-130] (0.5) | 1310 |
| 12 | Ex. 17* estolide (98) | Alkyl 3-(3',5'-di-t-butyl-4'-hydroxyphenyl) propionate [Na-Lube ® AO-242] (1) | Nonylated diphenylamine [Na-Lube ® AO-130] (1) | 965 |
| 13 | Ex. 17* estolide (98.2) | [Na-Lube ® BL-1208 Add Pack] (1.8) (44 wt. % of add pack contains 1:1 w/w of 2,6-di-t-butylphenol and nonylated diphenylamine) | | 1012 |
| 14 | Ex. 17* estolide (99.2) | [Na-Lube ® BL-1208 Add Pack] (0.8) (44 wt. % of add pack contains 1:1 w/w of 2,6-di-t-butylphenol and nonylated diphenylamine) | | 1292 |
| 15 | Ex. 14* estolide (99) | 2,6-di-t-butylphenol [Na-Lube ® AO-210] (0.5) | Nonylated diphenylamine [Na-Lube ® AO-130] (0.5) | 368 |
| 16 | Ex. 15A* estolide (98.2) | [Na-Lube ® BL-1208 Add Pack] (1.8) (44 wt. % of add pack contains 1:1 w/w of 2,6-di-t-butylphenol and nonylated diphenylamine) | | 687 |
| 17 | Ex. 15A* estolide (99) | 2,6-di-t-butylphenol [Na-Lube ® AO-210] (0.5) | Nonylated diphenylamine [Na-Lube ® AO-130] (0.5) | 574 |
| 18 | Ex. 15B* estolide (99) | 2,6-di-t-butylphenol [Na-Lube ® AO-210] (0.5) | Nonylated diphenylamine [Na-Lube ® AO-130] (0.5) | 190 |
| 19 | Bunge high oleic canola oil (100) | — | — | 15 |
| 20 | Bunge high oleic canola oil (99.5) | 2,6-di-t-butylphenol [Na-Lube ® AO-210] (0.25) | Nonylated diphenylamine [Na-Lube ® AO-130] (0.25) | 38 |

TABLE 14-continued

| Form. No. | Base Oil (wt. %) | Phenolic Antioxidant [tradename] (wt. %) | Amine Antioxidant [tradename] (wt. %) | RPVOT ASTM 2272-11 (mins) |
|---|---|---|---|---|
| 21 | Bunge high oleic canola oil (99) | 2,6-di-t-butylphenol [Na-Lube ® AO-210] (0.5) | Nonylated diphenylamine [Na-Lube ® AO-130] (0.5) | 52 |
| 22 | Bunge high oleic canola oil (98) | 2,6-di-t-butylphenol [Na-Lube ® AO-210] (1) | Nonylated diphenylamine [Na-Lube ® AO-130] (1) | 68 |
| 23 | Group ISN 250, 7.1 cSt (100) | — | — | 27 |
| 24 | Group I SN 250, 7.1 cSt (99.5) | 2,6-di-t-butylphenol [Na-Lube ® AO-210] (0.25) | Nonylated diphenylamine [Na-Lube ® AO-130] (0.25) | 420 |
| 25 | Group I SN 250, 7.1 cSt (99) | 2,6-di-t-butylphenol [Na-Lube ® AO-210] (0.5) | Nonylated diphenylamine [Na-Lube ® AO-130] (0.5) | 458 |
| 26 | Group I SN 250, 7.1 cSt (98) | 2,6-di-t-butylphenol [Na-Lube ® AO-210] (1) | Nonylated diphenylamine [Na-Lube ® AO-130] (1) | 434 |
| 27 | Group II Chevron 220R 6.6 cSt (100) | — | — | 43 |
| 28 | Group II Chevron 220R 6.6 cSt (99.5) | 2,6-di-t-butylphenol [Na-Lube ® AO-210] (0.25) | Nonylated diphenylamine [Na-Lube ® AO-130] (0.25) | 436 |
| 29 | Group II Chevron 220R 6.6 cSt (99) | 2,6-di-t-butylphenol [Na-Lube ® AO-210] (0.5) | Nonylated diphenylamine [Na-Lube ® AO-130] (0.5) | 444 |
| 30 | Group II Chevron 220R 6.6 cSt (98) | 2,6-di-t-butylphenol [Na-Lube ® AO-210] (1) | Nonylated diphenylamine [Na-Lube ® AO-130] (1) | 786 |
| 31 | Group II Chevron 220R 6.6 cSt (99.3) | [Na-Lube ® BL-1208 Add Pack] (0.7) (44 wt. % of add pack contains 1:1 w/w of 2,6-di-t-butylphenol and nonylated diphenylamine) | | 243 |
| 32 | Group III 7.2 cSt (100) | — | — | 82 |
| 33 | Group III 7.2 cSt (99.5) | 2,6-di-t-butylphenol [Na-Lube ® AO-210] (0.25) | Nonylated diphenylamine [Na-Lube ® AO-130] (0.25) | 604 |
| 34 | Group III 7.2 cSt (99) | 2,6-di-t-butylphenol [Na-Lube ® AO-210] (0.5) | Nonylated diphenylamine [Na-Lube ® AO-130] (0.5) | 836 |
| 35 | Group III 7.2 cSt (98) | 2,6-di-t-butylphenol [Na-Lube ® AO-210] (1) | Nonylated diphenylamine [Na-Lube ® AO-130] (1) | 1787 |
| 36 | PAO 4 cSt (100) | — | — | 20 |
| 37 | PAO 4 cSt (99.5) | 2,6-di-t-butylphenol [Na-Lube ® AO-210] (0.25) | Nonylated diphenylamine [Na-Lube ® AO-130] (0.25) | 868 |
| 38 | PAO 4 cSt (99) | 2,6-di-t-butylphenol [Na-Lube ® AO-210] (0.5) | Nonylated diphenylamine [Na-Lube ® AO-130] (0.5) | 1698 |
| 39 | PAO 4 cSt (98) | 2,6-di-t-butylphenol [Na-Lube ® AO-210] (1) | Nonylated diphenylamine [Na-Lube ® AO-130] (1) | 1452 |
| 40 | PAO 7 cSt (99) | 2,6-di-t-butylphenol [Na-Lube ® AO-210] (0.5) | Nonylated diphenylamine [Na-Lube ® AO-130] (0.5) | 1996 |
| 41 | PAO 7 cSt (99.3) | [Na-Lube ® BL-1208 Add Pack] (0.7) (44 wt. % of add pack contains 1:1 w/w of 2,6-di-t-butylphenol and nonylated diphenylamine) | | 1801 |
| 42 | FormulaShell ® 10W-30 "Clean Engine Formula" | Formulated, off-shelf motor oil (add-pack components and concentrations not determined) | | 130 |

TABLE 14-continued

| Form. No. | Base Oil (wt. %) | Phenolic Antioxidant [tradename] (wt. %) | Amine Antioxidant [tradename] (wt. %) | RPVOT ASTM 2272-11 (mins) |
|---|---|---|---|---|
| 43 | Mobil 1 5W-30 "Advanced Full Synthetic" | Formulated, off-shelf motor oil (add-pack components and concentrations not determined) | | 192 |
| 44 | Ex. 17* estolide (98) | 2,6-di-t-butylphenol [Na-Lube ® AO-210] (0.5) Nonylated diphenylamine [Na-Lube ® AO-130] (0.5) Ester/amide/carboxylate rust inhibitor [K-Corr ® 100] (1) | | 736 |

Example 19

Estolides were prepared according to the methods set forth above. To the resulting estolides were added various antioxidants and antioxidant-containing additive packages. Heat and stifling were applied where necessary to effect dissolution of the antioxidant and/or additive package in the estolide base oil. The oxidative stability of the resulting formulated estolides was then tested by the modified P-DSC test, wherein oxidation onset temperature (OT) was determined by non-isothermal pressurized-differential scanning calorimetry (P-DSC) under dynamic $O_2$ conditions (see, e.g., Dunn, "Effect of antioxidants on the oxidative stability of methyl soyate (biodiesel)," *Fuel Process. Tech.,* 86: 1071-85 (2005), incorporated herein by reference in its entirety for all purposes). Results for the various formulations are set forth below in Table 15, along with comparative testing results for various non-estolide containing base oil formulations.

TABLE 15

| Form. No. | Base Oil (wt. %) | Antioxidant [tradename] (wt. %) | P-DSC Average OT after three runs (° C.) |
|---|---|---|---|
| 1 | Ex. 15A* estolide (100) | — | 208 |
| 2 | Ex. 15A* estolide (99) | BHA (1) | 227 |
| 3 | Ex. 15A* estolide (99) | TBHQ (1) | 219 |
| 4 | Ex. 15A* estolide (99) | propyl gallate (1) | 231 |
| 5 | Ex. 15A* estolide (99) | BHT (1) | 221 |
| 6 | Ex. 15A* estolide (99) | Pyrogallol (1) | 235 |
| 7 | Ex. 15A* estolide (99) | α-tocopherol (1) | 212 |
| 8 | Ex. 15A* estolide (99) | Alkylated diphenylamines [Vanlube ® NA] (1) | 230 |
| 9 | Ex. 15A* estolide (99) | Octylated diphenylamines [Vanlube ® SL] (1) | 238 |
| 10 | Ex. 15A* estolide (99) | [Lubrizol ® 7652A add pack] (1) (add pack contains from 20-29.9 wt. % butylated phenol, and from 0.1-0.9 wt. % diphenylamine) | 229 |
| 11 | Ex. 15A* estolide (99) | [Elco ® 148P] (1) | 210 |
| 12 | Ex. 15A* estolide (99) | [Elco ® 8101] (1) | 225 |
| 13 | Ex. 15A* estolide (99) | [Elco ® 160] (1) | 212 |
| 14 | Ex. 15A* estolide (99) | Zinc dialkyl dithiophosphate [Elco ® 108] (1) | 219 |
| 15 | Ex. 15A* estolide (99) | Zinc dialkyl dithiophosphate [Elco ® 103] (1) | 214 |
| 16 | Ex. 15A* estolide (99) | Octylated/butylated diphenylamines [Irganox ® 57] (1) | 241 |

TABLE 15-continued

| Form. No. | Base Oil (wt. %) | Antioxidant [tradename] (wt. %) | P-DSC Average OT after three runs (° C.) |
|---|---|---|---|
| 17 | Ex. 15A* estolide (99) | Alkyl 3-(3',5'-di-t-butyl-4'-hydroxyphenyl) propionate [Na-Lube ® AO-242] (1) | 219 |
| 18 | Ex. 15A* estolide (99) | [Na-Lube ® BL-1208 Add Pack] (1) (44 wt. % of add pack contains 1:1 w/w of 2,6-di-t-butylphenol and nonylated diphenylamine) | 232 |
| 19 | Ex. 15A* estolide (99) | [Irgalube ® F 20] (1) | 219 |
| 20 | Ex. 15A* estolide (99) | $C_7$-$C_9$ branched alkyl 3-(3',5'-di-t-butyl-4' -hydroxyphenyl) propionate [Irganox ® L-135] (1) | 219 |
| 21 | Ex. 15A* estolide (99) | Octylated/butylated diphenylamines [Na-Lube ® AO-142] (1) | 236 |
| 22 | Ex. 15A* estolide (99) | Octylated phenyl-α-naphthylamine [Irganox ® L-06] (1) | 245 |
| 23 | Ex. 15A* estolide (99) | [Irganox ® L-150 Add Pack] (1) (Add pack contains 70 wt. % octylated/butylated diphenylamines, 15 wt. % thiodiethylene-bis-(3,5-di-t-butyl-4-hydroxyhydrocinnamate), and 15 wt. % tetrakis-(methylene-(3,5-di-t-butyl-4-hydrocinnamate)) methane | 239 |
| 24 | Ex. 15A* estolide (99) | Thiodiethylene-bis-(3,5-di-t-butyl-4-hydroxyhydrocinnamate) [Irganox ® L-115] (1) | 213 |
| 25 | Ex. 15A* estolide (99) | 2,6-di-t-butylphenol [Na-Lube ® AO-210] (0.5) Nonylated diphenylamine [Na-Lube ® AO-130] (0.5) | TBD |
| 26 | Ex. 17* estolide (99) | 2,6-di-t-butylphenol [Na-Lube ® AO-210] (0.5) Nonylated diphenylamine [Na-Lube ® AO-130] (0.5) | TBD |
| 27 | Valvoline 5W-30 | Formulated, off-shelf motor oil (add-pack components and concentrations not determined) | 246 |

*TBD = to be determined

Example 20

Estolides were prepared according to the methods set forth above. To the resulting estolides were added various antioxidants. Heat and stifling were applied where necessary to effect dissolution of the antioxidant and/or additive package in the estolide base oil. The oxidative stability of the resulting formulated estolides was then tested by the pressurized-differential scanning calorimetry (P-DSC) at various temperatures, with oxidation induction time (OIT) reported in minutes. Results for the various formulations are set forth below in Table 16.

TABLE 16

| Form. No. | Base Oil (wt. %) | Antioxidant [tradename] (wt. %) | Temp., ° C. | OIT, mins |
|---|---|---|---|---|
| 1 | Ex. 17* estolide (100) | — | 180 | 13 |

TABLE 16-continued

| Form. No. | Base Oil (wt. %) | Antioxidant [tradename] (wt. %) | Temp., ° C. | OIT, mins |
|---|---|---|---|---|
| 2 | Ex. 17* estolide (99) | 2,6-di-t-butylphenol [Na-Lube ® AO-210] (0.5) Nonylated diphenylamine [Na-Lube ® AO-130] (0.5) | 180 | 89 |
| 3 | Ex. 15A* estolide (99) | 2,6-di-t-butylphenol [Na-Lube ® AO-210] (0.5) Nonylated diphenylamine [Na-Lube ® AO-130] (0.5) | 180 | 42 |

TABLE 16-continued

| Form. No. | Base Oil (wt. %) | Antioxidant [tradename] (wt. %) | Temp., ° C. | OIT, mins |
|---|---|---|---|---|
| 4 | Ex. 17* estolide (99) | 2,6-di-t-butylphenol [Na-Lube ® AO-210] (0.5) Nonylated diphenylamine [Na-Lube ® AO-130] (0.5) | 155 | >120 |
| 5 | Ex. 15A* estolide (99) | 2,6-di-t-butylphenol [Na-Lube ® AO-210] (0.5) Nonylated diphenylamine [Na-Lube ® AO-130] (0.5) | 155 | >120 |

The invention claimed is:

1. A method of preparing an oxidatively stable estolide base oil, said method comprising selecting a first estolide base oil having an initial acid value;

reducing the initial acid value of the first estolide base oil to provide a second estolide base oil having an acid value of equal to or less than 0.5 mg KOH/g; and combining the second estolide base oil with at least one amine antioxidant to provide the oxidatively stable estolide base oil, wherein said oxidatively stable estolide base oil has a time of at least 700 minutes when tested in a rotating pressurized vessel oxidation test using ASTM Method 2272-11.

2. The method according to claim 1, wherein reducing the acid value of the first estolide base oil to provide the second estolide base oil comprises contacting said first estolide base oil with at least one acid-reducing agent.

3. The method according to claim 2, wherein the at least one acid-reducing agent is selected from one or more of activated carbon, magnesium silicate, aluminum oxide, silicon dioxide, a zeolite, a basic resin, or an anionic exchange resin.

4. The method according to claim 1, wherein the second estolide base oil has an acid value of equal to or less than 0.2 mg KOH/g.

5. The method according to claim 4, wherein the second estolide base oil has an acid value of equal to or less than 0.1 mg KOH/g.

6. The method according to claim 1, wherein the oxidatively stable estolide base oil has a time of at least 1000 minutes when tested in a rotating pressurized vessel oxidation test using ASTM Method 2272-11.

7. The method according to claim 1, wherein the second estolide base oil comprises at least one estolide compound selected from compounds of Formula I:

Formula I

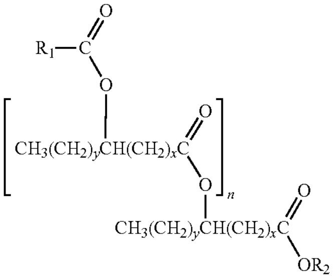

wherein x is, independently for each occurrence, an integer selected from 0 to 20;

y is, independently for each occurrence, an integer selected from 0 to 20;

n is an integer greater than or equal to 0;

$R_1$ is an optionally substituted alkyl that is saturated or unsaturated, and branched or unbranched; and $R_2$ is an optionally substituted alkyl that is saturated or unsaturated, and branched or unbranched, wherein each fatty acid chain residue of said at least one estolide compound is independently optionally substituted.

8. The method according to claim 7, wherein x is, independently for each occurrence, an integer selected from 1 to 10;

y is, independently for each occurrence, an integer selected from 1 to 10;

n is an integer selected from 0 to 8;

$R_1$ is an optionally substituted $C_1$ to $C_{22}$ alkyl that is saturated or unsaturated, and branched or unbranched; and $R_2$ is an optionally substituted $C_1$ to $C_{22}$ alkyl that is saturated or unsaturated, and branched or unbranched, wherein each fatty acid chain residue is unsubstituted.

9. The method according to claim 8, wherein x+y is, independently for each chain, an integer selected from 13 to 15; and n is an integer selected from 0 to 6.

10. The method according to claim 9, wherein x is, independently for each occurrence, an integer selected from 7 and 8.

11. The method according to claim 9, wherein y is, independently for each occurrence, an integer selected from 7 and 8.

12. The method according to claim 7, wherein $R_2$ is an unsubstituted alkyl that is saturated or unsaturated, and branched or unbranched.

13. The method according to claim 9, wherein $R_2$ is an unsubstituted alkyl that is saturated and branched or unbranched.

14. The method according to claim 13, wherein $R_2$ is selected from $C_6$ to $C_{12}$ alkyl.

15. The method according to claim 7, wherein $R_1$ is an unsubstituted alkyl that is saturated or unsaturated, and branched or unbranched.

16. The method according to claim 13, wherein $R_1$ is an unsubstituted alkyl that is saturated and branched or unbranched.

17. The method according to claim 1, wherein the at least one amine antioxidant is a diphenylamine antioxidant.

18. The method according to claim 17, wherein the at least one amine antioxidant is an alkylated diphenylamine antioxidant.

19. The method according to claim 18, wherein the at least one amine antioxidant is selected from one or more of a nonylated diphenylamine, an octylated diphenylamine, or a butylated diphenylamine.

20. The method according to claim 1, wherein the oxidatively stable estolide base oil consists essentially of the second estolide base oil and the at least one amine antioxidant.

21. The method according to claim 16, wherein the second estolide base oil consists essentially of the at least one estolide compound.

22. The method according to claim 21, wherein the second estolide base oil has an acid value of equal to or less than 0.2 mg KOH/g.

23. The method according to claim 22, wherein the oxidatively stable estolide base oil consists essentially of the second estolide base oil and the at least one amine antioxidant.

24. The method according to claim 23, wherein the oxidatively stable estolide base oil has a time of at least 1000 minutes when tested in a rotating pressurized vessel oxidation test using ASTM Method 2272-11.

* * * * *